US006506600B2

(12) United States Patent
Hermonat et al.

(10) Patent No.: US 6,506,600 B2
(45) Date of Patent: Jan. 14, 2003

(54) SECRETING PRODUCTS FROM SKIN BY ADENO-ASSOCIATED VIRUS (AAV) GENE TRANSFER

(75) Inventors: Paul L. Hermonat, Little Rock, AR (US); Michael Mane, Little Rock, AR (US); Yong Liu, Little Rock, AR (US)

(73) Assignee: University of Arkansas, Little Rock, AR (US)

(*) Notice: Subject to any disclaimer, the term of this patent is extended or adjusted under 35 U.S.C. 154(b) by 0 days.

(21) Appl. No.: 09/813,937

(22) Filed: Mar. 22, 2001

(65) Prior Publication Data

US 2002/0001580 A1 Jan. 3, 2002

Related U.S. Application Data

(60) Provisional application No. 60/191,092, filed on Mar. 22, 2000.

(51) Int. Cl.[7] ............................ C12N 5/02; C12N 15/63; C12N 15/11
(52) U.S. Cl. ..................... 435/371; 435/320.1; 435/366; 536/23.1; 536/23.2
(58) Field of Search .............................. 536/23.1, 23.2; 424/93.21; 435/371, 366, 325, 320.1

(56) References Cited

U.S. PATENT DOCUMENTS 4,868,116 A * 9/1989 Morgan et al. .......... 435/240.2

FOREIGN PATENT DOCUMENTS

| WO | WO 93/24641 A2 | 12/1993 |
| WO | WO 98/45462 A1 | 10/1998 |
| WO | WO 99/61601 A3 | 12/1999 |

OTHER PUBLICATIONS

Meyers, Organotypic (raft) epithelial tissue culture system for the differentiation–dependent replication of pappillomavirus, 1996, Methods in Cell Science, vol. 18, pp. 201–210.*
Walther et al., Viral vectors for gene transfer, 2000, Drugs, vol. 60, pp. 249–271.*
Braun–Falco et al.; "Efficient Gene Transfer into Human Keratinocytes with Recombinant Adeno–Associated Virus Vectors"; Gene Therapy; Stockton Press; vol. 6, No. 3; Mar. 1999; pp. 432–441.
Bantel–Schaal et al.; "Characterization of the DNA of a Defective Human Parvovirus Isolated from a Genital Site"; Virology; Academic Press, Inc.; vol. 134; May 1984; pp. 52–63.
Han et al.; "High Prevalence of Adeno–Associated Virus (AAV) Type 2 rep DNA in Cervical Materials: AAV May Be Sexually Transmitted"; Virus Genes; Kluwer Academic Publishers; vol. 12, No. 1; Feb. 1996; pp. 47–52.

Malhomme et al.; Human Genital Tissues Containing DNA of Adeno–Associated Virus Lack DNA Sequence of the Helper Virus Adenovirus, Herpes Simplex Virus of Cytomegalovirus but Frequently Contain Human Papillomavirus DNA; Journal of General Virology; SGM; vol. 78, Part 8; Aug. 1997; pp. 1957–1962.
Munster; "Cultured Skin for Massive Burns"; Annals of Surgery; Lippincott–Rave Publishers; vol. 224, No. 3; Sep. 1996; pp. 372–377.
Tobiasch et al.; "Detection of Adeno–Associated Virus DNA in Human Genital Tissue and in Material From Spontaneous Abortion"; Journal of Medical Virology; Wiley–Liss, Inc.; vol. 44, No. 2; Oct. 1994; pp. 215–222.
Walz et al.; "Defection of Infectious Adeno–Associated Virus Particles in Human Cervical Biopsies"; Virology; Academic Press; vol. 247, No. 1; 1998; pp. 97–105.
Meyers et al.; Ubiquitous Human Adeno–Associated Virus Type 2 Autonomously Replicates in Differentiating Keratinocytes of a Normal Skin Model:; Virology; Academic Press; vol. 272, No. 2; Jul. 2000; pp. 338–346.
Hermonat et al.; Adeno–Associated Virus Rep78 Inhibits Oncogenic Transformation of Primary Human Keraticocytes by a Human Papillomavirus Type 16–ras Chimeric; Gynecologic Oncology; Academic Press; vol. 66, No. 3; 1997; pp. 487–494.
Buller et al.; Herpes Simplex Virus Types 1 and 2 Completely Help Adenovirus–Associated Virus Replication; Journal of Virology; vol. 40, No. 1; 1981; pp. 241–247.
Zhu et al.; "Interaction of ATF6 and Serum Response Factor"; Molecular and Cellular Biology; vol. 17, No. 9; Sep. 1997; pp. 4957–4966.
Vogel; "Keratinocyte Gene Therapy"; Archives of Dermatology; vol. 129, No. 11; Nov. 1993; pp. 1478–1483.
Vincent Descamps et al., "Sustained Production of Erythropoletin in Mice by Human Keratinocytes Transduced with an Adeno–Associated Vector," British Journal of Heamatology, vol. 93, No. 2, 1996, p. 333 XP001064824.

* cited by examiner

Primary Examiner—Remy Yucel
Assistant Examiner—Sita Pappu
(74) Attorney, Agent, or Firm—Foley & Lardner

(57) ABSTRACT

The present invention utilizes AAV as a vector to transfect epithelial cells with an AAV/heterologous gene containing/Neo vector, to form a heterologous protein secreting culture of epithelial cells. This culture is useful for preparing recombinant skin using the organotypic epithelial raft culture system. The sheets of epithelial cells is composed of a stratified sqaumous epithelium composed of a lower layer of immature basal cells and an upper layer of mature keratinized epithelium. The rAAV virus stock prepared without wild type AAV is useful in expressing heterologous protein, however, the maximum production of the heterologous protein was achieved; when the rAAV virus stock contained wild type AAV. This invention discloses that AAV is appropriate for genetically altering skin to secrete new proteins to treat diseases and skin disorders or conditions.

27 Claims, 10 Drawing Sheets

SEQUENCE LISTING

<160> NUMBER OF SEQ ID NOS: 4

<210> SEQ ID NO 1
<211> LENGTH: 19
<212> TYPE: DNA
<213> ORGANISM: Unknown
<220> FEATURE:
<223> OTHER INFORMATION: glucose response element
<220> FEATURE:
<221> NAME/KEY: misc_feature
<222> LOCATION: (6)..(14)
<223> OTHER INFORMATION: "N" at positions 6 - 14 can be A, C, G or T

<400> SEQUENCE: 1
ccaatnnnnn nnnnccacg                                                19

<210> SEQ ID NO 2
<211> LENGTH: 15
<212> TYPE: DNA
<213> ORGANISM: Unknown
<220> FEATURE:
<223> OTHER INFORMATION: glucose response element
<220> FEATURE:
<221> NAME/KEY: misc_feature
<222> LOCATION: (7)..(9)
<223> OTHER INFORMATION: "N" at positions 7 - 9 can be A, C, G or T

<400> SEQUENCE: 2
cacgtgnnnc agctg                                                    15

<210> SEQ ID NO 3
<211> LENGTH: 20
<212> TYPE: DNA
<213> ORGANISM: Unknown
<220> FEATURE:
<223> OTHER INFORMATION: primer

<400> SEQUENCE: 3
gcaggcagaa gtatgcaaag                                               20

<210> SEQ ID NO 4
<211> LENGTH: 25
<212> TYPE: DNA
<213> ORGANISM: Unknown
<220> FEATURE:
<223> OTHER INFORMATION: primer

<400> SEQUENCE: 4
tgcaggaatt cagcacaaat tgtag                                         25

US 6,506,600 B2

SECRETING PRODUCTS FROM SKIN BY ADENO-ASSOCIATED VIRUS (AAV) GENE TRANSFER

BACKGROUND OF THE INVENTION

This application claims the benefit of Provisional application Ser. No. 60/191,092, filed Mar. 22, 2000.

STATEMENT AS TO THE RIGHTS TO INVENTION MADE UNDER FEDERALLY SPONSORED RESEARCH AND DEVELOPMENT

Part of the work performed during development of this invention utilized U.S. Government funds. The U.S. Government has certain rights in this invention.

FIELD OF THE INVENTION

The present invention is directed to a method for preparing epithelial cells, particularly keratinocytes, and more particularly, primary keratinocytes, containing an adeno-assoicated virus (AAV) vector containing a gene that encodes a heterologous protein and using these transfected cells to express the heterologous protein and secrete it from the cells. The transfected epithelial cells are useful for preparing a culture of these epithelial cells that secrete the heterologous protein. The cultures are composed of epithelial cells that express the heterologous protein, and are useful in preparing sheets of epithelial cells or recombinant skin composed of stratified squamous epithelium, that express the heterologous protein. This recombinant skin is useful in skin gene therapy, as a skin graft in a subject who is in need of the expressed heterologous protein to either treat a systemic disease or a specific skin disease.

DESCRIPTION OF THE RELATED ART

U.S. Pat. No. 4,868,116 prepared epithelial cells that expressed foreign genes by co-culturing keratinocytes and fibroblasts, also known as producer cells, that were treated to prevent their multiplication. The fibroblasts carried an infectious recombinant retrovirus containing the gene encoding the foreign gene. The keratinocytes were cultured to produce a sheet of keratinous tissue that expresses a hormone, an enzyme or a drug not normally expressed in keratinocytes. These sheets are said to be useful to graft onto subjects in need of the secreted products and to improve the general properties of the skin. However, the serious drawback of this disclosure is the use of a retrovirus as the vector to introduce the heterologous gene, which is now banned by the Food & Drug Admnistration, as a vector for gene therapy. Additionally, the co-culturing of the keratinocytes with fibroblast cells as a source of the recombinant retroviruses potentially introduces an additional cell into the skin graft that is not required in the present invention. The present invention is simpler and less dangerous as the retrovirus producer cells, the fibroblasts, are oncogenically transformed and may produce wild type (wt) retroviruses, which have been shown to produce lymphomas/leukemias. Additionally, the present invention does not select with G418 that stimulates terminal differentiation and dramatically limits the life span and growth of the keratinocytes in the skin sheets. Further, the prior art method utilizes the SV40 promoter, whereas the present invention preferably utilizes the AAV p5 and skin specific promoters, such as keratin specific promoters; for example, keratin 5 and keratin 14 promoters.

Braun-Falco et al. (20) discloses transducing human primary keratinocytes with an rAAV/LacZ construct that results in the presence of the rAAV/LacZ construct in up to 70% of human keratinocytes grown in culture. However, this study merely cultures keratinocytes, obtaining monolayers of keratinocytes, and did not produce recombinant skin that produces a heterologous protein as disclosed by the present invention. Although it is stated that rAAV shows promise as a gene transfer vehicle for skin gene therapy, there is no evidence that this system works in skin because these researchers did not produce skin. Recently several groups have found that AAV is able to infect the squamous epithelial tissues of the genital tract. (1, 4, 5, 6, 10, 16, 19).

SUMMARY OF THE INVENTION

It is an object of the present invention to produce epithelial cells containing an adeno-assoicated virus (AAV) vector containing a gene that encodes a heterologous protein.

It is an additional object of the present invention to culture the AAV transfected epithelial cells to produce a culture of epithelial cells that expresses the heterologous protein encoded by the gene.

It is a further object of the present invention to prepare recombinant skin that is an intact stratified squamous epithelium composed of these AAV transfected epithelial cells that secretes the heterologous protein for use in skin grafts to provide a subject with a source of the heterologous protein.

It is an additional object of the present invention to treat a subject in need of treatment by the expressed heterologous protein by contacting the skin of the subject with a sheet of AAV transfected epithelial cells or recombinant skin that expresses the heterologous protein into the skin of the subject.

DETAILED DESCRIPTION OF THE PREFERRED EMBODIMENTS

It has been recognized that skin is useful as an advantageous target for the correction of genetic disorders of secreted proteins or skin specific products. (3, 18) Skin cells are easily grown in tissue culture and the reimplantation of these cells, as epithelial cell sheet, back onto the patient is a standard therapy for treating burn patients in some institutions. (2, 11, 12, 13)

Figure 4:
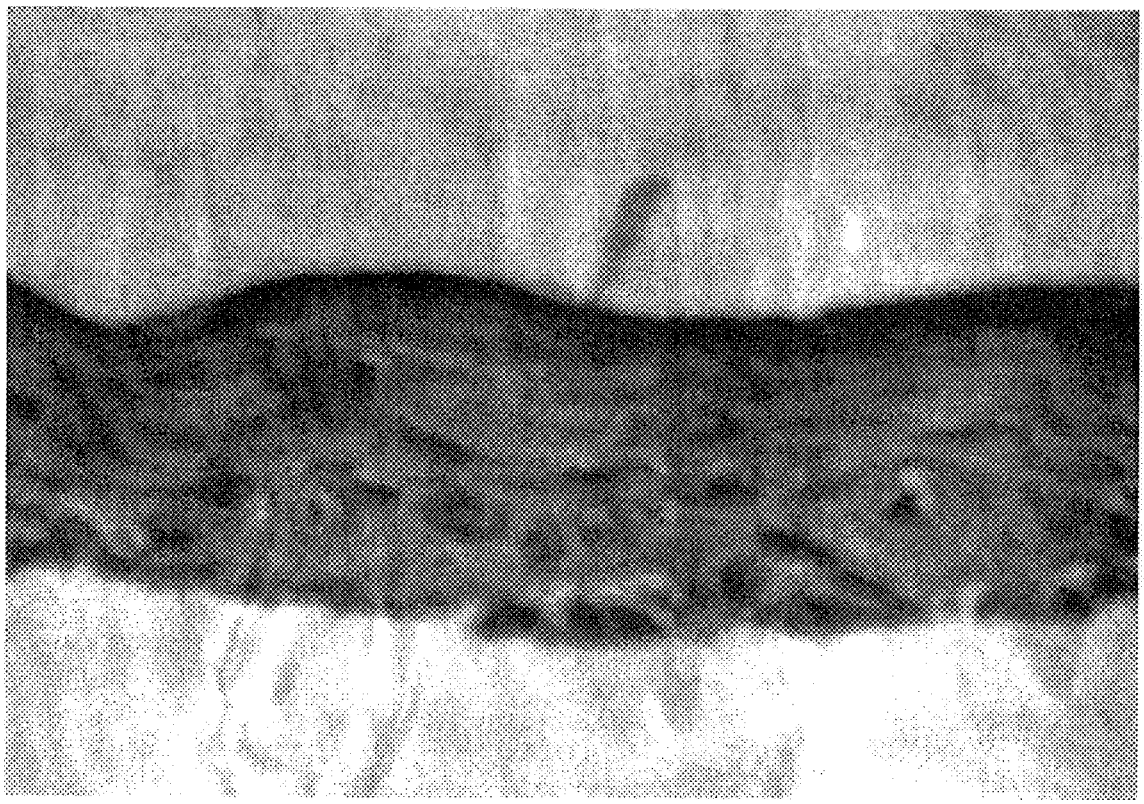
FIG. 4: Tissue culture skin histology demonstrates that the reagents used in the present invention result in a normal stratified squamous epithelium.

Genetically altered skin or recombinant skin is a useful platform for the in vivo generation of proteins which are needed systemically (secreted) or locally in the skin (eg. genetic disease of the skin). Recombinant skin or r-skin, within the context of the present invention, is a normal stratified squamous epithelium as shown in FIG. 4. It is composed of immature basal cells in the lower level closer to the body and mature kertanized eptithelium in the top layer. Because skin is an exposed organ it offers additional advantages in manipulation and safety. If the transgenic product being produced and secreted by the r-skin is at too high or low a level, the size of the r-skin graft can be increased or diminished appropriately. Furthermore, the exposed nature of the skin offers potential advantages for the regulation of the transgene by topically applied agents. Finally, skin gene therapy appears to be intrinsically safer than gene therapy at internal body sites as the r-tissue can be more easily monitored and treated (removed) than such internal sites.

The present invention is directed to the secretory production potential of genetically altered recombinant skin (r-skin). The r-skin is generated by first genetically altering primary human keratinocytes using adeno-associated virus (AAV) vectors. R-skin is generated from these altered keratinocytes using any method that produces skin from cultured cells, but preferably the organotypic epithelial "raft" culture system. The present invention also analyzes the r-skin's ability to secrete transgenic proteins in tissue culture and when grafted onto SCID mice.

AAV is used as the delivery vehicle because AAV is epithelial-tropic and AAV chromosomally integrates to give a stable long-term provirus. AAV is used as the delivery vehicle because AAV is epithelial-tropic and AAV chromosomally integrates to give a stable long-term provirus. AAV is a epithelial-tropic parvovirus (1, 4, 5, 6, 10, 16, 19, 21, 22). In the past AAV was considered a strict helper-dependent parvovirus which meant that the host cell must be coinfected with a member of the adenovirus (Ad) or herpesvirus (HSV and CMV) families in order for productive AAV infection to take place (23, 24). However it is now known that AAV is able to autonomously replicate in a model of normal skin, the organotypic epithelial "raft" culture system (21). However, under most other conditions AAV is still considered a helper-dependent parvovirus. When no helper virus is present, AAV readily (at 0.5% to 80% depending on a number of factors) latently infects the host cell by chromosomal integration and waits there for subsequent super-infection by a helper virus (25–28). Moreover, the proviral structure is stable for more than 100 cell divisions (29, 16). Very often the AAV provirus structure exists as concatemers (as many as 20 copies) of the AAV genome (29). Single copies occur as well. Although it is widely distributed, AAV has not been found to cause any disease.

Data shows significant secretion, both short-term and out to one month, of a cytokine transgene for granulocyte macrophage colony stimulating factor (GM-CSF) in r-skin by AAV-delivery. The present invention utilizes several promoters, including the AAV p5, skin specific and regulated promoters, to express the transgene. GM-CSF, insulin, and factor VIII are transgenes that the r-skin of the present invention secretes for use systemically to treat clinical diseases. The present invention provides AAV transfected epithelial cells, such as primary keratinocytes, that express a heterologous protein in culture.

These transfected epithelial cells are cultured into sheets of recombinant skin, and are useful, when grafted to a subject's skin, as a source of the heterologous protein. The transfection of basal epithelial cells with AAV vectors, are cultured and subsequently form a stratified squamous epithelium from these cells that then secrete a product at levels sufficient to treat the subject for a disease or skin condition. Diseases such as diabetes and hemophilia or other blood disorders are treated by the AAV transfected epithelial cells of the present invention. The present invention is useful in skin gene therapy. First, as skin is known to be a secretor of a variety of products, recombinant skin is used to replace the loss of secreted or systemic proteins due to genetic disease, such as the loss of human growth hormone. Second, skin gene therapy is used to treat skin specific genetic diseases, for example, skin pigmentation disorders, such as melanin disorder, or other skin diseases that could benefit from this therapy. Third, as many carcinomas develop in the skin, gene delivery of anti-cancer therapeutic genes are useful to treat these cancers. Fourth, skin gene therapy is useful for wound healing. The present invention relies upon the use of AAV as a vector to introduce the gene encoding the heterologous protein into epithelial cells. These epithelial cells express the heterologous protein in culture. These cells are then cultured to produce a sheet of epithelial cells that produces the heterologous protein and is useful as a skin graft in subject in need of the expressed heterologous protein. The skin graft is transferred to the subject using known methods (2, 11, 12, 13) and the AAV transfected epithelial cells of the skin graft express the heterologous protein that is useful in treating a condition of the patient.

The heterologous proteins that are expressed by the AAV transfected epithelial cells of the present invention include proteins or peptides that are normally produced by the human body, such as growth hormones, such as human growth hormone, granulocyte-macrophage colony stimulating factor (GM-CSF); plasma proteins, such as factor VIII and factor IX, insulin, glycogen storage proteins; enzymes; apolipoprotein E (apo E); and any systemic proteins, such hormones, cytokines or proteins or peptides that are not normally produced by the human body, such as proteins for skin treatment or cancer treatment.

The present invention will be useful for the expression of GM-CSF for the treatment of neonatal and adult neutropenia/leukopenia or chemotherapy induced leukopenia: Neutropenia, low neutrophil counts, in neonates is often associated with sepsis, prematurity and maternal hypertension with increased risk of mortality. Adults can also develop neutropenia for a number of reasons such as exposure to toxic chemicals, such as during chemotherapy (30–34). Both clinical situations can be effectively treated by injected GM-CSF. For example, in one study the neutrophil count was raised in all patients suffering from neutropenia due to chemotherapy treated by GM-CSF, by the median of 6.6-fold (35). The neutrophil level of $1.0 \times 10^9/L$ was reached after two weeks of treatment. The initial dose of GM-CSF was 5 microg/kg/day, and 1–7 microg/kg/day was required to maintain the neutrophil level above $1.0 \times 10^9/L$. Premature neonates also suffer from neuro/leukopenia, simply because their immune systems are immature. (30,36,37). In one study 75 neonates (25 small for gestational age) <32 weeks gestation were randomized to receive GM-CSF ($10 \mu g/kg/d$) by subcutaneous injection for 5 days from <72 hours after birth. This treatment, completely abolished neutropenia in treated infants, when both well and septic, throughout the period of study (36).

GM-CSF expressed according to the present invention in r-skin is useful for the treament of pulmonary alveolar proteinosis. Pulmonary alveolar proteinosis (PAP) is a lung disease characterized by the accumulation of lipoproteinaceous material within the alveoli making breathing difficult. Reduced GM-CSF production may be involved in the pathogenesis of PAP. In one study GM-CSF replacement was used to treat PAP in four patients (38). Subcutaneous GM-CSF was self-administered once daily for 12 wk (dose escalation from 3 to 9 $\mu g/kg/d$). Response was assessed by measuring symptoms, arterial blood gas measurements, pulmonary function testing, and chest radiographs. Three of the four patients experienced symptomatic, physiologic, and radiographic improvement with the GM-CSF treatment. Increased oxygenation was also observed but was not apparent until 8 to 12 wk after the start of therapy. Therefore, GM-CSF appears to benefit a subset of patients with adult PAP and may represent an alternative to whole-lung lavage or lung transplantation in treating the disease. Systemic, constitutive expression of GM-CSF could lead to even more significant improvements.

Additionally, the expression of insulin in the r-skin of the present invention for the treatment of type 1 diabetes. Pancreatic beta cells release insulin under high serum glucose levels to regulate glucose levels by stimulating glucose uptake by the liver. Type 1 diabetes, lack of insulin expression, is a result of beta cell death in patients. These patients must monitor their glucose levels and be self-treated with exogenous insulin, by subcutaneous injecton, to maintain a stable level of glucose. This reactionary methodology is of limited effectiveness, and the vast majority of Type 1 diabetics ultimately develop a wide range of secondary symptoms (blindness, heart disease, etc.) and suffer from increased mortality. The ideal form of treatment would seem to be a replacement gene therapy which mimics the original regulation of insulin by the beta cells. As many (if not all) tissues have glucose regulated gene expression, insulin may be regulated by glucose-responsive pathways in these other tissues, for example hepatocytes (39).

There are a number of glucose response regulatory pathways in cells. For example, Yoshida et al. (1999) have identified a DNA motif (CCAATN9CCACG SEQ ID NO:1) which, then located within a promoter, conferred glucose responsiveness to promoters (40). The putative transcription factor which bound this element was ATF6. ATF6 is expressed in at least some epithelial cells (41) and may be expressed in keratinocytes. Another glucose responsive element are the "E boxes" (CACGTGN3CAGCTG SEQ ID NO:2) which are present in the rat glucagon receptor gene promoter, the glucose 6-phosphatase promoter, and others (42,43). It may be important that the correct network of transcription factors and cellular mileu are present in keratinocytes and the ligation of these elements into the AAV p5 promoter with subsequent testing for glucose responsiveness is encompassed by the present invention.

Even without a glucose regulating promoter, it is widely believed that a low level secretion of insulin may convert a Type 1 diabetic into a more manageable Type 2 diabetic. This type of gene therapy, promoting constitutive expression, is achieved by the r-skin of the present invention, thus, mimicking the approach taken for generating skin for secreting GM-CSF.

Factor VIII expressed according to the present invention is useful for the treatment of hemophilia A. Hemophilia A is a bleeding disorder due to an X-linked inherited deficiency of factor VIII. It is the most common of the congenital coagulation disorders, occurring 1/10,000 males (and the occasional homozygous female). Clotting can be severely prolonged with dramatic, severe consequences that are only mitigated by provision of factor VIII. In those patients with factor VIII levels below 5% of normal, spontaneous bleeding can occur and severe bleeding after minor injury is common. Infusion of factor VIII can control bleeding but must be repeated frequently as its half-life in blood is 12 hours. Clearly treatment of this disorder would be greatly enhanced by a therapeutic modality that raised and maintained factor VIII levels into at least the low end of normal (10%).

Furthermore, abridged factor VIII genes are small but fully functional, and as with full-length factor VIII, discussed above, also is a candidate for expression in the r-skin of the present invention. Normal human factor VIII is a proteolytically processed glycosylated protein of about 350 kDa in size. Although the full length factor VIII cDNA is too large (7 Kb) to insert into virus vectors, an abridged version, constructed by Toole, et al (1986), is fully functional in clotting activity (17). In fact, the abridged factor VIII gene is more active in producing clotting activity than the wild type gene by over 10 fold. This appears to be the result of the abridged factor VIII gene allowing for 10 fold higher levels of secretion of the factor VIII molecule (17). The abridged factor VIII coding sequence is only 4.4 kb in length and produces a product of 160 kDa in size, by deletion of most of the "B" domain of that molecule. This abridged gene is small enough for insertion into virus vectors. The abridged factor VIII cDNA is substituted for full-length factor VIII or any of the other DNA sequences encoding the heterologous proteins for construction of AAV vectors for use in transducing skin cells.

Furthermore, the present invention also includes manipulations that regulate and increase the epithelial cell secretory abilities by expressing the recombinant gene from a strong promoter. The heterologous gene is operably linked to the promoter and it is important that the promoter is functional in the epithelial cells so that the heterologous protein is expressed. Promoters useful in the present invention are strong promoters, such as the SV40 early enhancer/promoter, AAVp5 or skin specific promoters, such as the keratin K14 promoter or keratin K5 promoter. The preferred promoters are AAV promoters or skin specific promoters.

The present invention is directed to a novel gene therapy approach for diseases involving systemic or blood borne products, or for genetic diseases of the skin. The ultimate use of this invention is to transduce the patients own keratinocytes with the therapeutic gene, culture the cells to form sheets, and graft these sheets back onto the patient. Such grafted cells re-establish a basement membrane (3) and become a histologically normal autologous skin graft. The graft secretes the therapeutic protein into the circulation through the basal cell layer, and basement membrane. There are numerous advantages to this approach. For example, the keratinocytes are efficiently and stably transduced using vectors derived from AAV. Secondly, the area of grafted skin can be adjusted to insure that the adequate amount of product is being secreted. Thirdly, skin grafting is a flexible system that can be used to introduce a variety of critical genes, such as factor VIII, insulin, GM-CSF, human growth hormone, parathyroid hormone, or possibly any gene whose product is secreted. Genetic diseases of the skin itself can also be treated by this methodology. Lastly, the transduced gene can potentially be regulated by diffusible transactivating substances applied topically to the grafted skin.

Skin grafts composed of AAV transfected epithelial cells of the present invention are feasible sources of a number of proteins that are useful to treat systemic diseases or specific skin conditions, as discussed above. A heterologous protein that can be expressed by the epithelial cells of the present invention is factor VIII. Factor VIII serum levels are estimated to range from 10 to 200 ngs per ml (7, 9). Factor VIII levels >10% of normal are thought to correct the most severe form of hemophilia (i.e. 1–20 ngs/ml). This assessment of skin graft feasibility is based upon the demonstration that 1 $cm^2$ of in vitro grown human keratinocytes grafted onto nude mice resulted in about 30 ngs per ml of human apolipoprotein E (apo'E) in the blood (3). This secretory capacity is useful to approximate a genetically altered skin secreting the wild type factor VIII gene product. Additionally it should be noted, however, that skin does not appear to be a strong expresser of apo'E (it secretes only about 1% of total body production). Useful in the present invention is an abridged factor VIII gene, which over-secretes its product by a factor of 10 over that of the wild type gene (17). As the difference in volume/weight between mouse and man is 10-4, and estimating that abridged factor VIII secretion is 10-fold over apo'E , then a 1,330 $cm^2$, or 206 $inch^2$, factor VIII secreting skin graft will treat an adult human (20 ngs/ml). The true normal level of factor VIII in the blood is unknown, however it is quite low. Some estimates run as low as 10 ugs per liter (10 ngs/ml) (7). A small skin graft of 1 or 2 $inches^2$ may be sufficient to provide 1 ng/ml. Furthermore, secretion of factor VIII or any other heterologous protein can be improved by expressing the recombinant gene from a strong promoter, such as the SV40 early promoter or the keratin K14 promoter.

Depending upon the expression levels of heterologous protein from the skin grafts and the levels of protein needed to treat the disease caused by the deficiency, a small graft of less than 50 $inch^2$, is sufficient to provide a beneficial effect. That only reasonably sized grafts are needed for significant serum levels of products introduced by this method is further supported by another study (15). In this study keratinocyte grafts (1–2 cm2) on nude mice, virally transduced with the human growth hormone (hGH), resulted in about 0.4–1.5 ng/ml in the blood. This figure translates to about 1,300 ngs/ml of blood of the abridged factor VIII protein when the longer half life (t1/2 12 hrs vs 4 mins) and increased molecular weight (160 vs 22 kDa) of factor VIII are accounted. This is 40 fold over the apo'E levels found above (3). Fenjves et al's studies (3) also demonstrated that molecules as large as apo'E (90 kDa) could easily diffuse from the skin graft, through the underlying basement membrane and stroma, and into the blood (3).

Skin grafting based gene therapy allows for greater control, regulation and manipulation of the skin implant and its expression than gene therapy through internal tissues. Using skin implants for gene therapy has several advantages over gene therapy through internal tissues, such as regulating the dose of the secreted product by regulating the square area, or amount of the implant. If the implant secretes too much of the product, then part or all of the implant can be removed. Furthermore, the exposed nature of the skin offers potential advantages for the regulation of the transgene by topically applied agents. For example, if the AAV recombinant vector includes a promoter which is regulatable by a diffusable factor (eg. a GRE responsive promoter, then the inserted gene will be regulated by application of the diffusable factor upon the surface of the implant. This technique provides for many exciting regulatory possibilities which would not be practical, or at least have many more complications, when using gene therapy through internal sites. Skin gene therapy may be intrinsically safer than gene therapy at internal body sites as the recombinant skin or tissue can be more easily monitored, treated and/or removed than at internal body sites.

The optimization of AAV-based transduction of keratinocytes to provide high levels of transgene delivery and a variety of transgene expression schemes resulting in constitutive or regulated expression is an important aspect of the present invention. The present invention demonstrates that rAAV is able to infect and transduce keratinocytes with the GM-CSF gene in an adequately efficient manner so as to allow significant product secretion. But the present invention is also directed to improving the transduction levels by altering conditions of infection and determining the best cellular targets, and then studying the resulting transduction efficiency. To achieve long term expression in the skin, stem cells must be transduced and the present invention emcompasses techniques for enriching for skin stem cells. One stem cell marker may simply be the size of the keratinocyte (44). But for keratinocytes smaller is better; i.e., smaller has the most growth potential. Another useful marker is integrin α6 (45).

In addition to improving skin cell transduction by optimized infection conditions, the ability to select for transduced skin cells is another way to generate high levels of gene transfer. Unfortunately, the NeomycinR/G418 selection technique induces keratinocytes to terminally differentiate. ThusI, the present invention does not use this normally excellent selection scheme. Rather, the present invention compares other marker gene/agent schemes and evaluates their suitability for selecting transduced keratinocytes without inducing differentiation. These markers, include for example, the Zeocin/Sh ble gene, 0.4 kb; L-histidinol/hisD gene, 1.3 kb; Blasticidin/bsd gene, 0.4 kb; hygromycin/ hygromycin-B-phosphotransferase gene/1.3 kb). The hisD gene has already been shown to be useful in selecting keratinocytes, but it is the largest of this set of marker genes and thus has a disadvantage (46).

Furthermore, keratinocytes are a cell type which always seem to be trying to terminally differentiate as they are being cultured. The present invention evaluates the use of agents that regulate keratinocyte differentiation and promote keratinocyte proliferation in conjunction with AAV transduction. Agents which promote keratinocyte differentiation also evaluated to determine the state of differentiation on rAAV transduction and the potential of non-stem cell transduction for transient expression in keratinocytes.

The choice of vector and particularly the choice of promoter driving the transgene affects expression in the keratinocytes and the r-skin of the present invention. The present invention compares a series of skin-specific promoters with the natural AAV p5 promoter (which may be another type of skin-favored promoter).

The present invention also evaluates the ability to generate inducible provirus in the disclosed system. The reason for this is that the expression of certain genes, such as insulin, do not require continuous expression. Furthermore the secretion of certain gene products may be hazardous or unpleasant (such as IL-2). Inducible promoters, such as, for example, are analyzed in the keratinocytes: steroid, tetracyclin, and glucose.

The present invention employs different therapeutic genes of different sizes in an effort to fully evaluate the capabilities of skin gene therapy. Also, using different sized genes allows the r-skin system to be used to secrete various sized products from skin and evaluate the upper size limit for the secretion of products by the skin. Fenjves et al demonstrated that molecules as large as apo'E (90 kDa) could easily diffuse from the skin graft, through the underlying basement membrane and stroma, and into the blood (1). Finally, AAV is a vector in which the proviral DNA can be in several alternative forms. Classically, AAV is known to chromosomally integrate. Wild type AAV integrates on a specific region on chromosome 19, while rAAV integrates in a roughly random manner. However, AAV can also survive as an episomal element in certain cell types. AAV provirus can also exist as concatemeric multimers, either episomal or integrated. Some forms suggest that AAV may partially replicate through a "rolling circle" mechanism. AAV is also a single stranded DNA genome most likely which must be converted to a double stranded version, episomal or integrated, prior to transcriptional expression. Clearly, chromosomal integration is the most ideal proviral state for stable long term expression in transduced keratinocyte and the keratinocytes of the present invention in culture and in the r-skin are evalueated for evidence of chromosomal integration.

EXAMPLES

Materials and Methods

Generation of Recombinant AAV/GM-CSF/Neo Virus Stocks

The wild type AAV genome pSM620 (14) was partially digested with Bsa I so as to delete the internal AAV sequences from map units 6 to 95 (nt 286–4460) and a specially designed polylinker was ligated in place, resulting in the AAV vector plasmid dI6-95/PL1. Into this polylinker the Neomycin resistance gene (Neo) and human granulocyte macrophage-colony stimulating factor (GM-CSF)(ATCC) gene were sequentially ligated. In the resulting plasmid, dI6-95/GM-CSFP$^5$/Neo$^{SV40}$ (hereafter referred to as AAV/ GM-CSF/Neo), the GM-CSF gene was expressed from the AAV p5 promoter while Neo was expresses from the SV40 early promoter which was present on in the Neo fragment.

Two types of virus stocks were generated, each in a two step process. To generate an initial virus stock 4 μgs of the AAV vector plasmid was lipofected with 0.5 μgs of the large wild type-plus AAV complementor plasmid ins96-0.8 (8) into adenovirus infected 293 cells (multiplicity of infection [MOI] of 5). After 24 hours the medium was removed and replaced with AIM-V medium (Gibco/BRL, Grand Island, N.Y.). This virus stock was then used to generate high producer cell lines. To do this 293 cells were infected with the initial virus stock (0.5 ml) and then placed under G418 selection (600 μgs/ml). After 10 days resistant colonies were picked and expanded, with continuous G418 selection. Equivalent numbers of cells from each producer clone were compared for their ability to generate replicative AAV/GM-CSF/Neo DNA. The cells were infected with adenovirus (MOI 5) for two hours. Then, 0.5 μg of ins96-0.8 plasmid was DEAE-dextran transfected into the cells. After 30 hours DNA was isolated by the method of Hirt, and the levels of replicating vector DNA analyzed by agarose gel electrophoresis and Southern blotting using $^{32}$P-labeled Neo DNA as a probe.

Two types of virus stocks were generated from these producer cell lines. One type was a very high titer AAV/ GM-CSF/Neo virus stock which also contains a significant wild-type AAV contamination. To generate this stock, the best producer cell line was infected with adenovirus at an MOI of 5 for two hours and then lipofected with 1 μg of ins96-0.8 plasmid. After 48 hours the cells were frozen and thawed three times to lyse the cells, heated to 56° C. to kill adenovirus helper, and filtered to remove cellular debris. The virus stock was then frozen at −80° C.

A second type of virus stock contained only AAV/GM-CSF virus. To generate this stock, the best producer cell line was infected with adenovirus at an MOI of 5 for two hours and then lipofected with 5 µg of opSH3 plasmid. The plasmid pSH3 contains all of the AAV and adenovirus genes needed to complement a fully defective rAAV genome such as AAV/GM-CSF/Neo. After 72 hours the cells were frozen and thawed three times to lyse the cells and filtered to remove cellular debris. The virus stock was then frozen at −80° C.

To titer the virus stock 10 µls were first treated with 100 units of DNase I/ml for 1 hour (Sigma Corp., cat. # D5025) (to destroy unencapsilated viral genomes). The DNase I was then inactivated by heating to 65° C. for 30 minutes. To isolate the virion DNA the virus stock was then digested with Proteinase K (0.5 mg/ml), phenol extracted, and ethanol precipitated. A series of known standardized amounts of AAV/GM-CSF/Neo plasmid, plus the DNA isolated from the virus stock, were then applied to a nylon membrane. Dot blotting was carried out as using known methods. Briefly, the DNA, in 5 µls of water, was first denatured by the addition of 10 µls of 0.4 N NaOH, incubated for 10 minutes, re-neutralized by the mixing of 200 µls of Tris/HCl (pH 7.0), 1.5 M NaCl, then immediately adding the solution to a dot blot apparatus under suction. The blot was then probed with $^{32}$P-labeled GM-CSF DNA. Comparing the signal strength of the unknown virus stock with the known standards determined the titer in encapsilated genomes/ml.

Keratinocyte and Skin Tissue Culture

Human primary foreskin keratinocytes (HPFK) were purchased from Clonetics (Walkersville, Md.) and maintained in Keratinocyte Serum Free Medium (Gibco, BRL). HPFK were mock infected, or infected with various amountss of the corresponding AAV/GM-CSF/neo recombinant virus stocks on the 10 cm tissue culture plates. After four hours of incubation at 37° C. cells were washed three times with PBS, detached from the plate using 0.025 mM tripcin/EDTA and placed on the top of collagene/fibroblast matrices in E media. After 4 hours collagene rafts with attached HPFK on it's surface were lifted onto the stainless steel grids, and the epithelial cells were fed by diffusion from under the matrix as previously described (21). Rafts were treated with 10 µM 1,2-dioctanoyl-sn-glycerol (C8; Sigma Chemical Co., St. Louis, Mo.) in 2 ml E medium every 24 hours. Collected 24 hours medium were analyzed or frozen for further analysis.

GM-CSF analysis by ELISA 100 µl of 24 h culture medium were subjected to ELISA assay according to the manufacturers instruction (Chemicon, Calif.).

Keratinocytes Infected with AAV/GM-CSF/Neo

Figure 1:
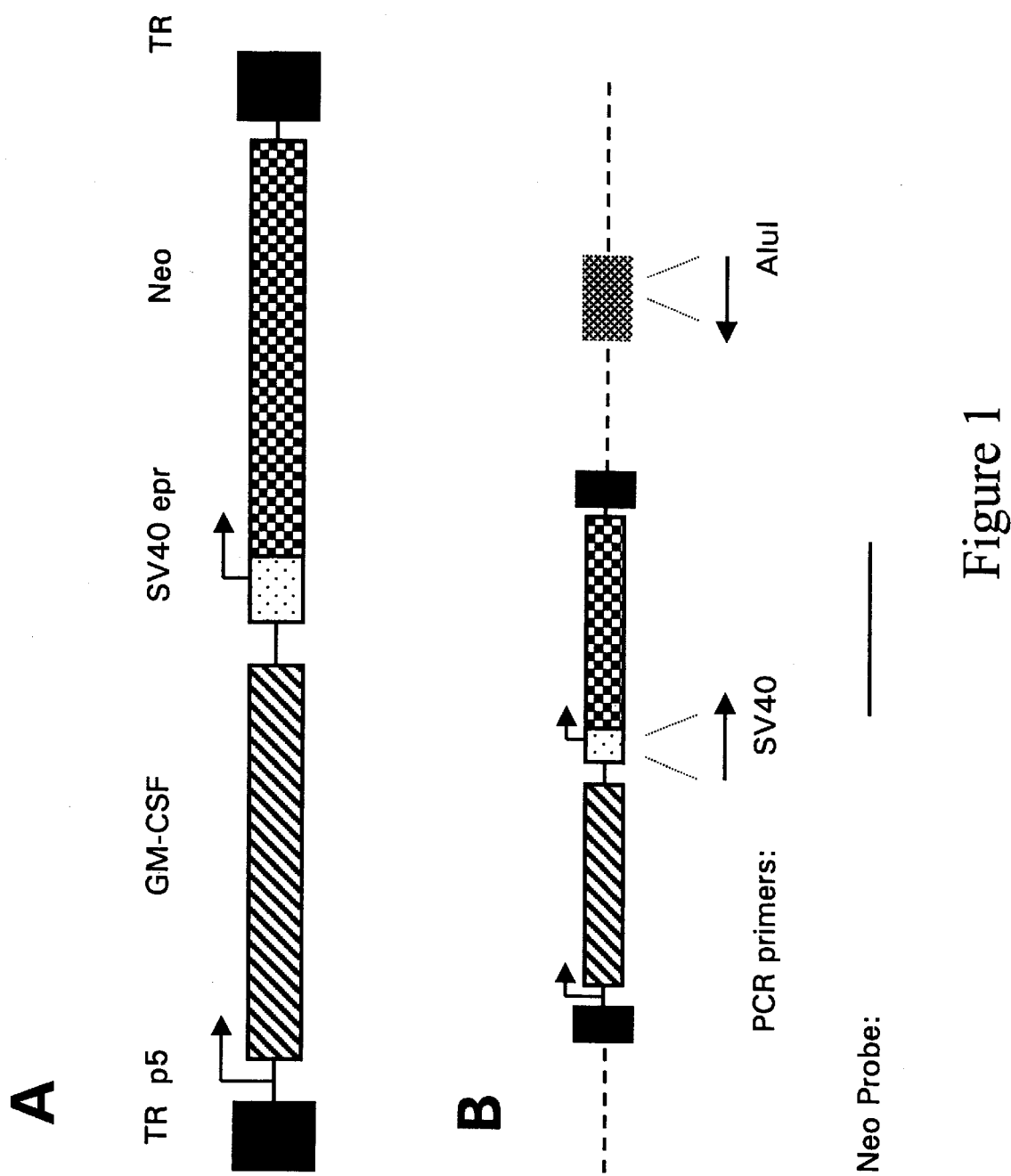
FIG. 1 shows the map of the AAV/GM-CSF/Neo virus vector, primer/probe design, production and characterization of AAV/GM-CSF/Neo virus stock. A shows a structural map of the dl6-95/GM-CSFP$^5$/Neo$^{SV40}$ virus with the names of the components at the top. TR (black box) refers to the AAV terminal repeats. P5 (bent arrow) refers to the AAV p5 promoter. The cross hatched box is the GM-CSF open reading frame. SV40 epr (stipled box/bent arrow) refers to the simian virus 40 early enhancer/promoter. The checkered box is the Neo open reading frame. To the right of the viral genome is a dot line which represents human chromosomal DNA and a gray box which represents an Alu I repetitive element. B Below the structural map is shown the location of the PCR primers and the probe used to demonstrate chromosomal integration in FIG. 5.
Figure 3:
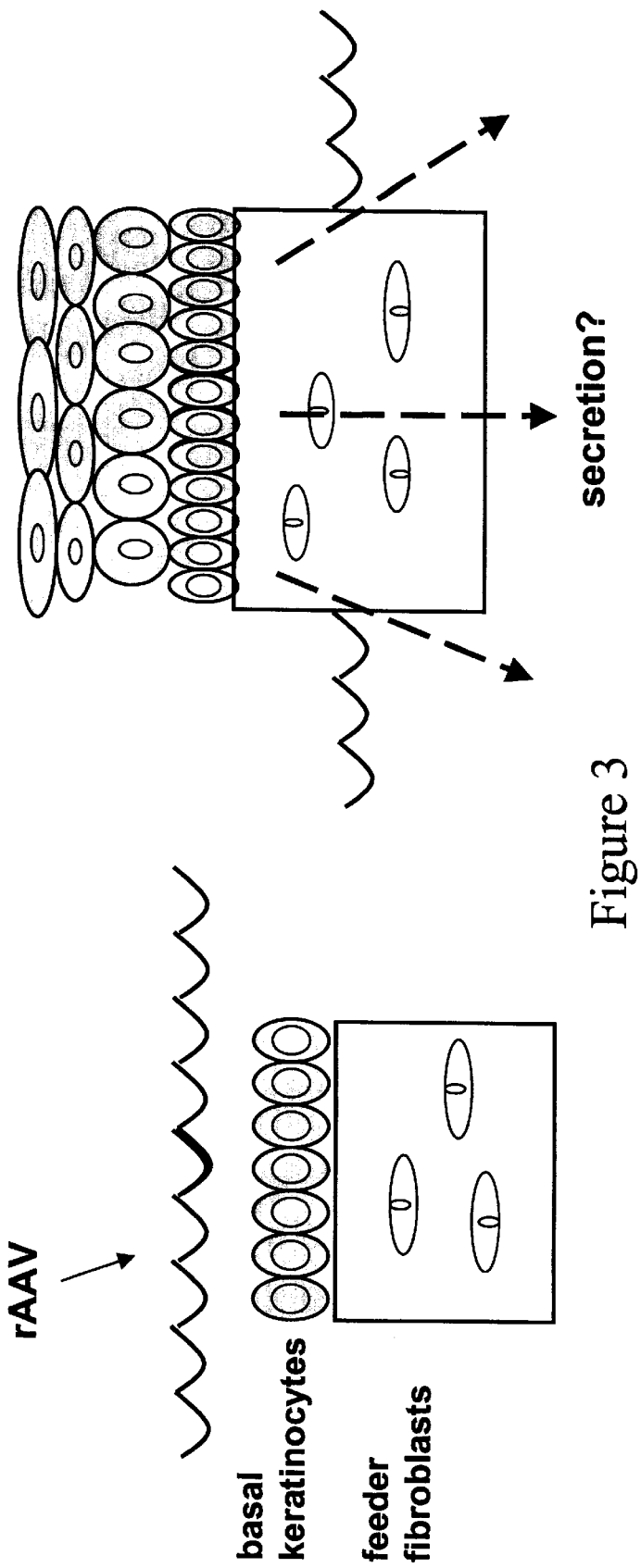
FIG. 3: Process of keratinocyte infection and tissue generation. Keratinocytes were infected with AAV/GM-CSF/Neo virus applied to the collagen raft, and raised to the air. At various times medium was withdrawn and analyzed for GM-CSF protein.

The present invention shows that keratinocytes infected with an AAV/GM-CSF/Neo vector as depicted in FIG. 1, are able to form a GM-CSF secreting skin using the organotypic epithelial raft culture system as shown in FIG. 3.

FIG. 4 shows that the reagents utilized in culturing the cells result in normal stratified squamous epithelium.

Figure 5:
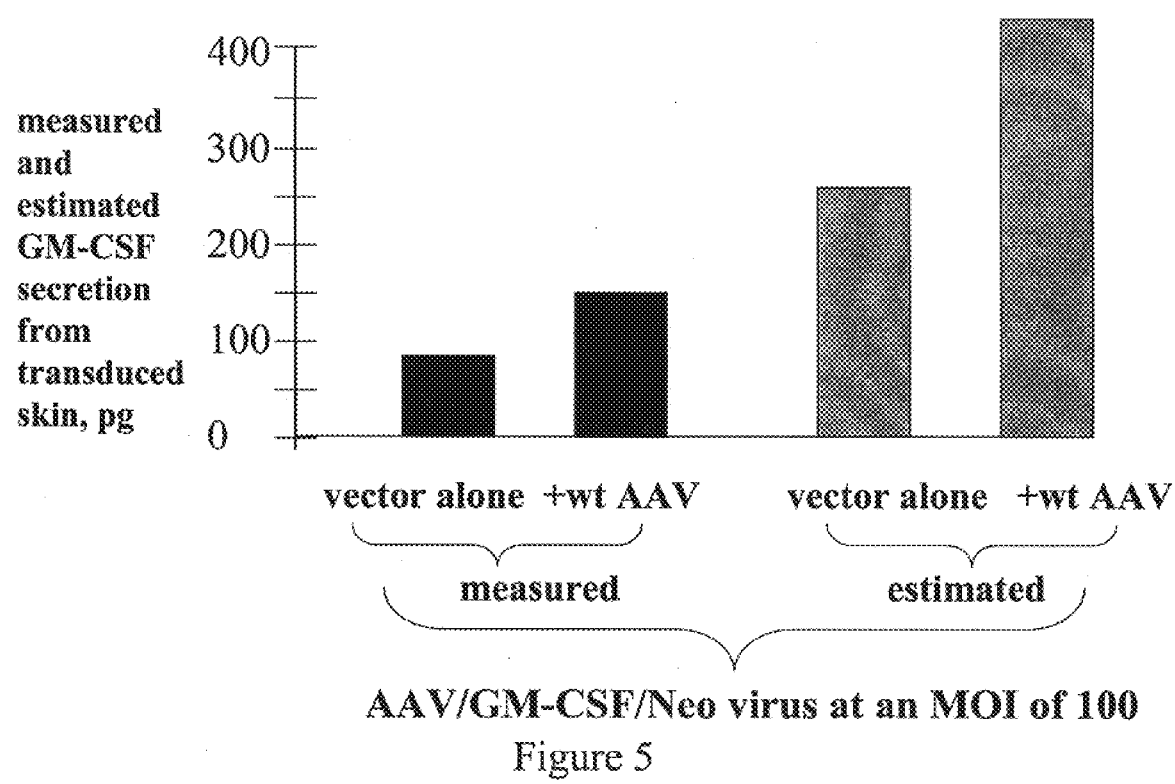
FIG. 5: Comparison of secretory activity of keratinocytes infected with AAV/GM-CSF/Neo virus with and without wild-type AAV. Keratinocytes were infected with 500 μls of each type of AAV/GM-CSF/Neo virus stock, and then used in an organotypic raft. Medium was collected over a 48 hour period, from days 2–3, and analyzed for GM-CSF protein by ELISA.

When the rAAV virus stock is prepared without wild type AAV the maximum production of GM-CSF was about 80 pg of GM-CSF per cm$^2$ of skin over a 48 hour period, days 2–3 post-infection. However, when the rAAV virus stock contained wild type AAV the production of GM-CSF was much higher at about 130 pg per cm2 of skin. As CM-CSF has a serum half-life of only 8 hours, it is likely that much higher levels of GM-CSF are actually secreted and these levels are shown on the right of FIG. 5, as "estimated" levels. These data as shown in FIG. 5, show that AAV is appropriate for genetically altering skin to secrete new proteins. Furthermore, the enhancement of activity by wild type AAV show that some form of complementation is taking place.

Figure 6:
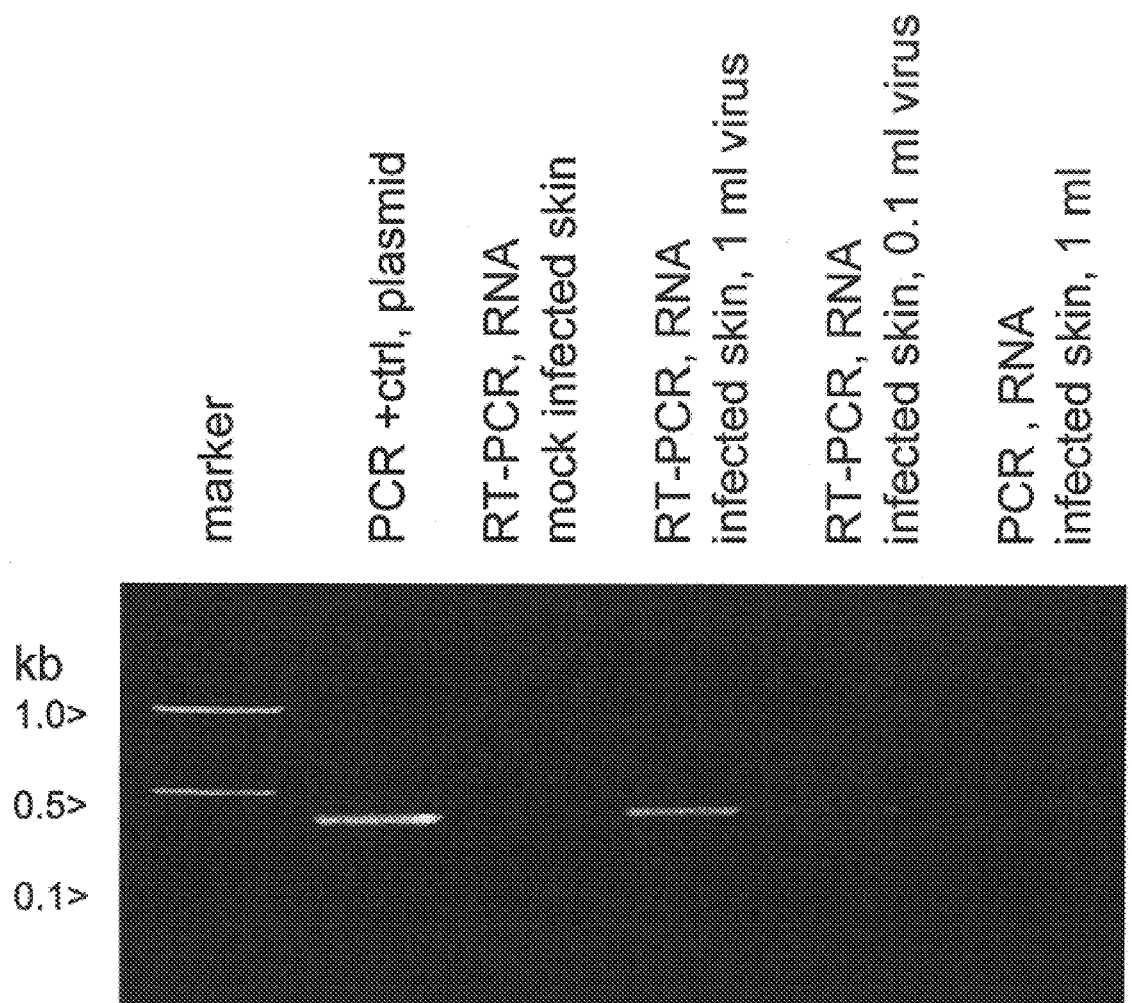
FIG. 6: GM-CSF RNA expression in the skin. Rafts generated with AAV-GM-CSF/Neo virus plus wild-type AAV, as in FIG. 4, were analyzed for GM-CSF RNA expression by reverse transcriptase-polymerase chain reaction (RT-PCR).

FIG. 6 shows the results of rafts generated with AAV-GM-CSF/Neo virus plus wild-type AAV were analyzed for GM-CSF RNA expression by reverse transcriptase-polymerase chain reaction (RT-PCR). The results show that virally infected skin produced GM-CSF RNA, while uninfected skin did not. Also PCR, alone, did not generate a band indicating that the signal seen was a specific measurement of RNA.

Figure 7:
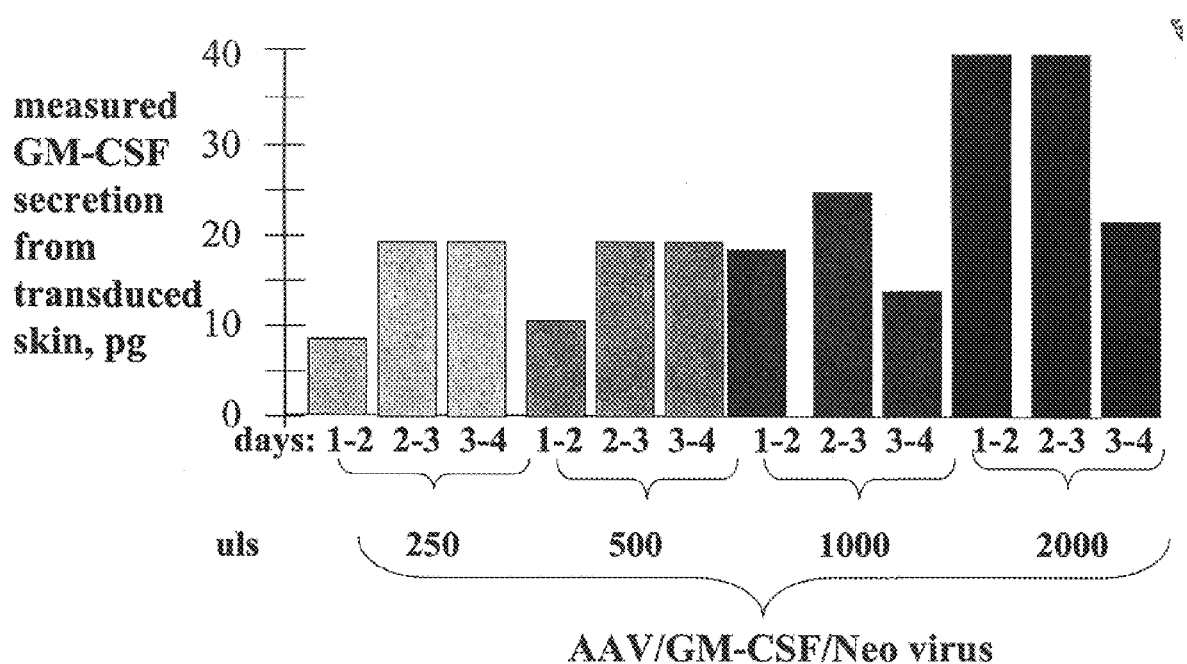
FIG. 7: GM-CSF secretion of time at various MOIs. Keratinocytes were infected with several amounts of pure AAV/GM-CSF/Neo virus and then rafts generated. Medium was removed at 24 hour intervals and analyzed for GM-CSF secretion.
Figure 8:
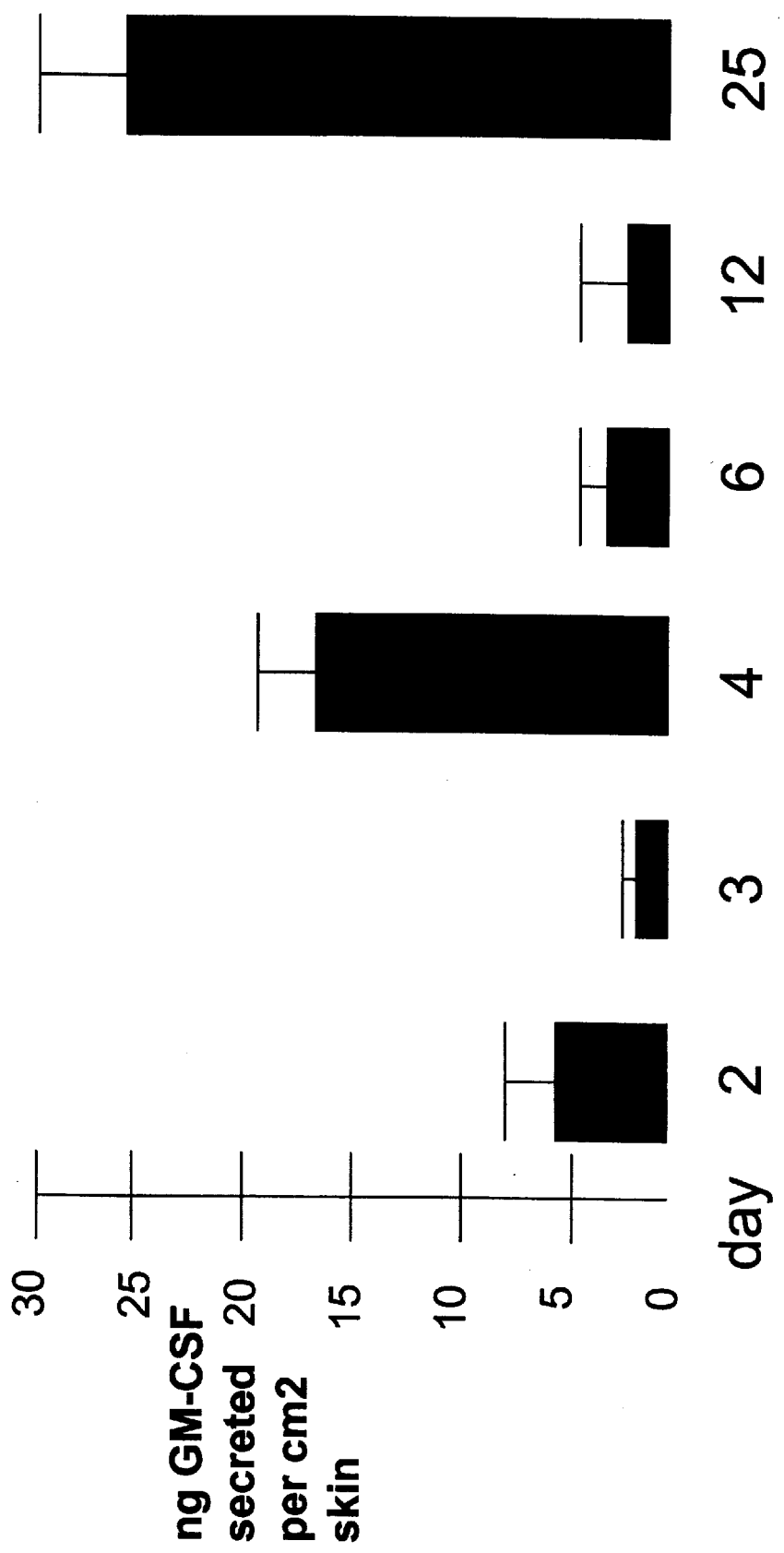
FIG. 8: Short and long-term secretory activity of keratinocytes infected with AAV/p5-GM-CSF/Neo. $2 \times 10^5$ keratinocytes were infected with 220 μls of AAV/p5-GM-CSF/Neo virus stock and then a skin raft was generated. The experiment was done in triplicate (3 rafts). At various times post-infection medium was removed and analyzed for GM-CSF by Sandwich ELISA. As three rafts were we have included a mean and standard deviation for each time point. These numbers are GM-CSF levels as measured so that the estimated GM-CSF actual secretion levels should be much higher due to GM-CSF's short half life.
Figure 9:
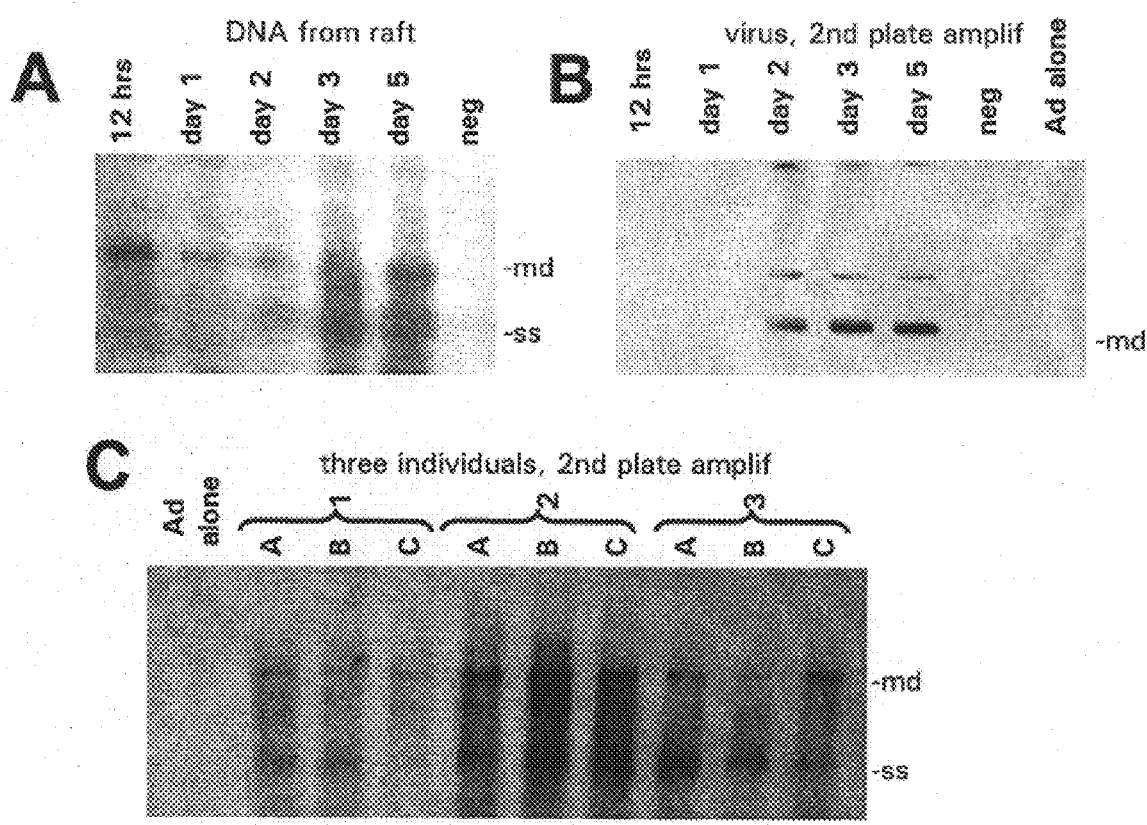
FIG. 9: Time course experiment of AAV infection in normal skin showing de novo, autonomous AAV replication and virus production. Epithelial raft tissues were AAV infected and generated with an AAV MOI of 10. Total DNA and putative AAV virus stocks were prepared and analyzed. Tissues were harvested at 12 hr, and days 1, 2, 3, and 5 post-infection. A. Southern blot measuring AAV DNA levels at increasing times post-infection; representative of three such experiments. Each lane represents 40% of the total DNA isolated from the tissues. The last lane represents mock infected tissues (neg). The AAV monomer duplex (md) is indicated on the right. B. Southern blot measuring AAV virus production in the same rafts as in A, after second plate amplification in adenovirus infected SW13 cells. Each lane represents 5% of Hirt extracted DNA. The last 2 lanes represents mock infected tissues (neg) and adenovirus alone 2nd plate amplification, respectively. The AAV monomer duplex (md) is indicated. C. Epithelial raft tissues generated from three different individuals, each done in triplicate, and each infected at time 0 with an AAV MOI of 20. Putative AAV virus stocks were prepared and amplified in a second plate of SW13 cells as in FIGS. 1, and 2B. Each lane represents 5% of Hirt extracted DNA.
Figure 10:
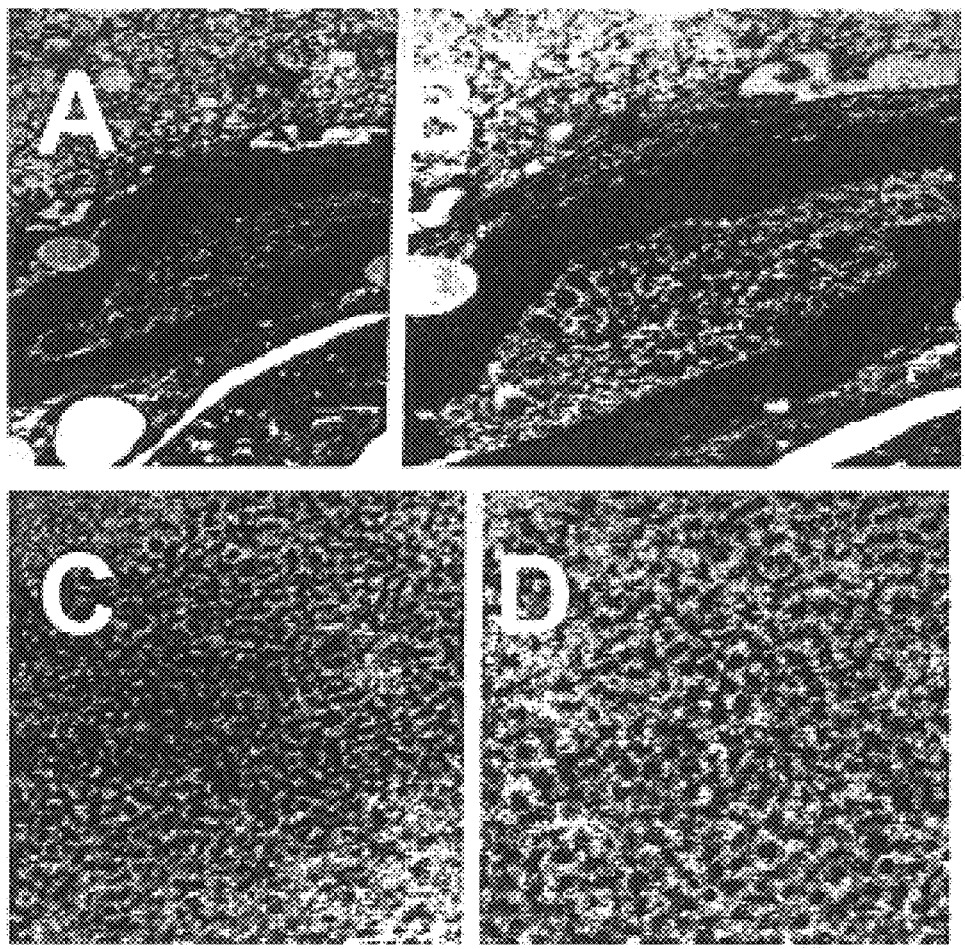
FIG. 10: Examination of primary raft epithelial tissues by electron microscopy for the presence of autonomously replicating AAV. AAV-infected primary epithelial raft tissue were allowed to grow and fully differentiate for 10 days, then were fixed with glutaraldehyde and stained with uranyl acetate. Numerous AAV particles averaged 26 nm in diameter were observed in nuclei of the epithelial granular cell layer. A. A representative nucleus with patches of virions. B. A higher magnification of A showing virions. C and D. Higher magnification views of the virions in A and B.

FIG. 7 shows GM-CSF secretion of time at various MOIs. Keratinocytes were infected with several amounts of pure AAV/GM-CSF/Neo virus, and then rafts generated. Medium was removed at 24 hour intervals and analyzed for GM-CSF secretion. The secretion of GM-CSF is relatively stable over 4 days at the 2 lowest infection levels. Suprisingly, at the higher levels of virus infection the GM-CSF secretion drops on days 3–4.

Experiments to Optimize Keratinocyte Transduction

The present invention encompasses methods for preparing keratinocytes which optimize transduction, growth and expression of heterologous proteins. The experiments described herein analyze the transduction efficiency as conditions are varied. It order to achieve long term expression in the skin stem cells must be transduced. The skin stem cells are thought to be the smallest keratinocytes and small keratinocytes have the highest proliferative potential. As such, the smallest keratinocytes are the primary target and are sorted. When the studies do not require long term expression, then transient expression is desirable.

Use of Skin Specific and Inducible Promoters:

Different skin specific promoters are selected and specifically, those promoters that provide maximum expression. It is believed that a promoter which expresses through all layers of the skin is a preferable choice. But a consideration is that maximum expression at the lower levels of the skin allows for maximum levels of product diffusion into the stroma below. Transduction is assayed using a variety of marker genes.

EXPERIMENT 1

This experiment is a large experiment in which multiple variables are tested for their ability to improve AAV transduction of keratinocytes. The efficiency of rAAV transduction of general keratinocyte cultures using assays specific for marker genes alkaline phosphatases (AP), LacZ (beta-galactosidase), and GM-CSF is analyzed. Transduction levels are monitored using the well characterized histochemical assays for AP (alkaline phosphatase) and LacZ (β-galactocidase) and results are scored as percent positive cells. Transduction levels for GM-CSF are measured as the amount of GM-CSF which is secreted into the medium by sandwich ELISA. The experimental variables of infection that are analyzed for improving keratinocyte transduction, include:

A) variable rAAV multiplicities of infection (MOI). Higher MOI generally result in higher transduction rates.

B) multiple rAAV infections. Multiple infections generally result in higher transduction rates., C) treatment of keratinoctyes with compounds (Amiloride [Sigma, St. Louis, Mo.] Amphiregulin [R&D Systems, Minneapolis, Minn.]) that inhibit differentiation and/or stimulate proliferation during transduction. Amiloride is a blocker of non-specific cation channels in keratinocytes, and is known to inhibit keratinocyte differentiation (47). Such channels are known to be upregulated during keratinoctye differentiation (48). Amphiregulin is a member of the epidermal growth factor family and promotes keratinocyte growth (49). Intrinsic to this activity we believe it is also must inhibit keratinocyte differentiation. A combination of Amiloride and Amphiregulin will also be assayed for improving rAAV transduction.

D) treatment of keratinocytes with a compound (Ca) that enhance differentiation during transduction. Undifferentiated, rapidly growing keratinocytes are the best targets. But analysis on differentiated keratinocytes also are studied. Calcium is the best studied agent for inducing keratinocyte differentiation.

The following subexperiments which correspond to A-D above:

Sub-Exper A, Variable MOI: A series of general keratinocyte cultures ($2 \times 10^5$) in 35 mm plates will be infected with increasing amounts ($10^5$, $10^6$, $10^7$, $10^8$, $10^9$ encapsidated genomes) of AAV/AP/Neo and the cells stained for AP activity at 3 and 7 days. A series of identically treated plates are infected with AAV/LacZ virus in place of AAV/AP/Neo and analyzed for AP activity. The percent of total keratinocytes found to be transduced are determined and compared. Transduction levels as determined by the expression of the transgene generally rise with increasing amounts of virus. But, in some cases, a plateau affect at the highest levels was seen. A series of identically treated plates are infected with AAV/LacZ virus or AAV/p5-GM-CSF/Neo in place of AAV/AP/Neo and analyzed for transgene activity.

Sub-Exper B, Multiple Infections: A series of general keratinocyte cultures ($2 \times 10^5$) in 35 mm plates are infected three times with $10^7$ encapsidated genomes of AAV/AP/Neo on days 0, 1, and 2 or days 0, 2, and 4 and stained for AP activity at days 3 and 7. A series of identically treated plates are infected with AAV/LacZ virus or AAV/p5-GM-CSF/Neo in place of AAV/AP/Neo and analyzed for transgene activity.

Sub-Exper C, Agents Inhibiting Differentiation: A series of general keratinocyte cultures ($2 \times 10^5$) in 35 mm plates are treated with 0.01, 0.1, 1, and 10 $\mu$M Amiloride (Sigma, St. Louis) or 0.01, 0.1, or 1 $\mu$g/ml Amphiregulin (R&D Systems, Minneapolis), while being infected with $10^7$ encapsidated genomes of AAV/AP/Neo and analyzed for AP activity at days 3 and 7. A combination of 0.1 $\mu$M Amiloride plus 0.1 $\mu$g Amphiregulin are also tried and compared to the rate of transduction of each component individually to observe if a synergistic transduction rate results. A series of identically treated plates are infected with AAV/LacZ virus or AAV/p5-GM-CSF/Neo in place of AAV/AP/Neo and analyzed for transgene activity.

Sub-Exper D, Agent Promoting Differentiation: A series of general keratinocyte cultures ($2 \times 10^5$) in 35 mm plates are treated with 0.001, 0.01, 0.1, 1, and 10 $\mu$M Calcium Chloride while being infected with $10^7$ encapsidated genomes of AAV/AP/Neo virus and analyzed for AP activity on days 3 and 7. A series of identically treated plates are infected with AAV/LacZ virus or AAV/p5-GM-CSF/Neo in place of AAV/AP/Neo and analyzed for transgene activity.

Primary human foreskin keratinocytes: Primary human foreskin keratinocytes are purchased from Clonetics/Bio Whittaker, San Diego, Calif. (catolog number NHEK-Neo).

Generation of rAAV plasmids. AAV/AP vector plasmid was obtained from Dr. Dusty Miller (50) and AAV/p5-LacZ and AAV/p5-GM-CSF/Neo vector plasmids are constructed (51). Human GM-CSF, insulin (mature version), and factor VIII (non abridged) were obtained from the American Type Culture Collection. Standard recombinant DNA methodologies are used for the other vector plasmids and and well known to persons skilled in the art. However, briefly, the AAV p5 based vectors are based on the AAV plasmid dI6-95 (51) and the second generation vectors in which new promoters (type 1 and type 2) are used in place of p5 and are based on the AAV plasmid dI3-94 (43), which has the p5 promoter deleted.

Generating and titering rAAV virus stocks. High titer virus stocks are generated in a two step process. To generate an initial virus stock 4 □gs of the AAV vector plasmid are lipofected with 4 $\mu$gs of the AAV/adenovirus complementor plasmid pSH3 (52) into 293 cells. Complementing plasmid pSH3 are used because it contains all of the AAV and adenovirus genes needed to complement AAV and generate rAAV virions. Furthermore the use of pSH3 does not generate wild type or pseudo-wild type AAV as a side product from to recombination. At 3 days post-infection these cells are frozen and thawed three times to generate a rough virus stock. This virus stock was then used to generate high producer cell lines. To do this 293 cells are infected with the initial virus stock (0.5 ml) and then placed under G418 selection (600 $\mu$gs/ml). After 10 days resistant colonies were picked and expanded, with continuous G418 selection. Equivalent numbers of cells from each producer clone are compared for their ability to generate replicative rAAV DNA. The cells are infected with adenovirus and wild type AAV (MOI 5). After 30 hours DNA are isolated by the method of Hirt (53), and the levels of replicating vector DNA analyzed by agarose gel electrophoresis and Southern blotting (54) using $^{32}$P-labeled gene insert DNA as a probe. The highest signal indicates the best producer cell line.

Those rAAV which do not carry a Neo gene (eg. AAV/p5-factor VIII) are generated by carrying out only the first step, DNA transfection, to produce a virus stock without generating a producer cell line. If the virus needs to be of a higher titer, a concentrate of the virus is produced using one of several affinity column technologies available (eg. Heparan). To generate high titer rAAV virus stocks, the best producer cell line are transfected with 10–20 $\mu$g of pSH3 complementor plasmid. After 12 hours the Dulbeccoe's Modified Eagles Medium is replaced with Life Technologies/Gibco (Gaithersburg, Md.) This step limits the amount of calcium in the resulting virus stock which can lead to keratinocyte terminal differentiation. After 72 hours the cells are frozen and thawed three times to lyse the cells and filtered to remove cellular debris. The virus stocks are then frozen at −80° C. If for some reason the virus must be concentrated or purified, affinity column (eg. Heparan) is used.

To titer the virus stock, 10 $\mu$ls is first treated with 100 units of DNase I/ml for 1 hour (Sigma Corp., cat. # D5025)(to destroy unencapsidated viral genomes). The Dnase I then us inactivated by heating to 65° C. for 30 minutes. To isolate the virion DNA, the virus stock is digested with Proteinase K (0.5 mg/ml), phenol extracted, and ethanol precipitated. A series of known standardized amounts of vector plasmid, plus the DNA isolated from the virus stock, are then applied to a nylon membrane. The dot blotting is carried out as described previously (6, 55) Briefly, the DNA, in 5 $\mu$ls of water, is first denatured by the addition of 10 $\mu$ls of 0.4 N NaOH, incubated for 10 minutes, re-neutralized by the mixing of 200 μls of Tris/HCl, pH 7.0, then the total solution is immediately added to a nylon membrane inserted into a dot blot apparatus under suction. The blot is then probed with $^{32}$P-labeled GM-CSF DNA. Comparing the signal strength of the unknown virus stock with the known standards will determine the titer in encapsidated genomes/ml.

Histochemical colorimetric staining for AP: Observation of transduced AP gene activity is readily accomplished by assays in widespread use. There are a variety of commercially available kits which allow for colorimetric determination of AP expressing cells. A variety of these kits are available from Sigma (St. Louis) and give resulting products of yellow, red, blue, or purple depending upon the specific kit (Sigma cat. no. 85L-1, 85L-2, 85L-3R, 86-R, 86-C).

Histochemical colorimetric staining for LacZ. LacZ/β-galactosidase marker gene are equally useful for observing transduced cells. Two weeks later, after forming definitive colonies, the cells are stained with X-gal and ferro-/ferri cyanide using strandard methodologies (56). The B-gal transduced PHFKs stain a deep blue and thus colonies, and even individual positive cells, are counted.

Measurement of GM-CSF secretion by ELISA. The secretion of GM-CSF into the medium are measured by a sandwich ELISA kit per kit instructions (Chemicon International, Inc., Temecula, Calif., Cat. No. CYT210).

EXPERIMENT 2

This experiment analyzes the efficiency of rAAV transduction of general keratinocyte cultures compared to keratinocyte stem cells sorted by α6 integrin subunit expression and small size.

Selection of keratinocyte stem cells by size. It has been reported that keratinocytes of less than 10 μM have significant growth potential. These cells will be sorted from the general population. Keratinocytes are trypsinized and resuspended at a concentration of approximately $10^6$/ml in Keratinocyte Serum Free Medium. Cells are sorted similar to Blantin et al (1999) (84) using FACS Vantage Cell Sorter (Becton Dickinson) cells are gated according to their forward and side scatter to the pulse width of the right angle scattered light.

A series of size sorted (< or =10 μM versus >10 μM ) and general keratinocyte cultures ($2\times10^5$) in 35 mm plates are infected $10^7$ encapsidated genomes of AAV/AP/Neo on days 0, 1, and 2 or days 0, 2, and 4 and stained for AP activity at days 3 and 7. A series of identically treated plates are infected with AAV/LacZ virus in place of AAV/AP/Neo and analyzed for LacZ activity.

Selection of keratinocyte stem cells by integrin alpha 6 sorting. Mouse antibody 4F10 (IgG2b)(Serotec) to the α6 integrin subunit are used at 20 μg/ml in conjunction with anti-mouse IgG2b-fluorescein isothiocyanate (FITC) to stain the keratinocyte stem cells for sorting. Keratinocyte cultures will be treated with 10 mM EDTA PBS and centrifuged. These cells are then processed for single FITC staining. The cells are resuspended in Keratinocyte Serum Free Medium at $2-3\times10^6$/ml, sorted using the Becton Dickinson FACStarPlus, and collected into tissue culture medium for plating and further experimentation.

A series of integrin alpha 6 sorted and general keratinocyte cultures ($2\times10^5$) in 35 mm plates are infected $10^7$ encapsidated genomes of AAV/AP/Neo on days 0, 1, and 2 or days 0, 2, and 4 and stained for AP activity at days 3 and 7. A series of identically treated plates are infected with AAV/LacZ virus in place of AAV/AP/Neo and analyzed for LacZ activity.

EXPERIMENT 3

This experiment analyzes the ability to select transduced keratinocytes (selectable marker genes Sh ble or bsd) with cytotoxic agents while maintaining growth potential with and without treatment with Amiloride (anti-differentiation).

The present invention has generated r-skin with significant secretory capabilities even without selecting for a pure population of transduced cells. However, the ability to select only successfully transduced cells would allow the generation of fully transduced keratinocyte populations and r-skin. There are a variety of resistance gene/selective agent systems available today, such as (G418/NeomycinR gene, 1.0 kb in size (58; Zeocin/Sh ble gene (59), 0.4 kb; L-histidinol/hisD gene, 1.3 kb (46); Blasticidin/bsd gene, 0.4 kb (60); hygromycin/hygromycin-B-phosphotransferase gene/1.3 kb). Unfortunately the grandfather selection agent, G418, stimulates terminal differentiation in primary keratinocytes (58), and in most cases, is not useful in the present invention. The hisD gene/L-histidinol system is the only selective system successfully used in keratinocytes without the strong induction of differentiation. This experiment tests various selective systems and observes the proliferative capacity of selected cells. Although all of the selectable marker genes in the experiment are tested, the Sh ble or bsd genes are particularly interesting because of their small size (0.4 kb).

Construction of vector plasmids. The vectors are constructed by generating the marker gene coding sequences by PCR amplification using commercial and common plasmids as templates and then ligating them down stream of the p5 promoter in dl6-95. Virus stocks are then generated as described above. Equivalent MOIs (encapsidated genomes) of each marker virus are used to infect general keratinocyte cultures and at 24 hours post-infection the appropriate cytotoxic agent is added. The selection is allowed to continue for 2–3 weeks and the cells fixed with formaldehyde and stained with methylene blue. The number of resistant colonies are counted and compared as an indicator of general compatability with keratinocytes. The most important phenotype, however, is the number of cells in the resistant colonies and their apparent cell size. The differences are analyzed by the naked eye, and if necessary by cell sizes and numbers by FACS analysis as in experiment 2. The experiment is repeated with the addition of 1 μM Amiloride and compatibility of the agent is observed with the selection scheme to determine if Ameloride is able to help in generating selected high-proliferative capacity keratinocyte colonies.

EXPERIMENT 4

This experiment analyzes the efficiency of rAAV vectors for GM-CSF, insulin, and factor VIII for transduction of keratinocytes using intracellular staining.

Intracellular staining for transgene products. This protocol is adapted from that described by Pala et al. (61). Transduced keratinocyte are tested at days 3, 6, 14, and 21 post infection. Keratinocytes are harvested, washed and fixed with 2% paraformaldehyde in PBS for 20 min at room temperature. The cells are then washed and permeabilized with PBS/1% BSA/0.5% saponin (S-7900, Sigma) for 10 min at room temperature. Activated and control cells are stained with FITC-anti-GM-CSF, FITC-anti-insulin, or FITC-anti-factor VIII and analyzed by flow cytometry.

EXPERIMENT 5

This experiment analyzes the efficiency of rAAVp5-GM-CSF and insulin transduction of keratinocytes using an ELISA assay for secreted transproduct. Keratinocytes are transduced under optimal conditions identified in Experiments 1–4

Measurement of GM-CSF secretion by ELISA. The secretion of GM-CSF into the medium are measured by a sandwich ELISA kit per kit instructions (Chemicon International, Inc., Temecula, Calif., Cat. No. CYT210).

Measurement of insulin secretion. Insulin levels in medium are measured by radio-immunoassay (RIA) (CIS, Biointernational, Gif-Sir-Yvette, France).

Measurement of factor VIII secretion. The factor VIII activity levels are measured using the Stachrom VIII:C kit manufactured by American Bioproducts Corp.

EXPERIMENT 6

This experiment describes the construction of second generation-type 1 vectors with the AAV p5 promoter replaced with skin specific promoters for the basal layer (K5), suprabasal (HPV-16 p97) and spinous/granular (involucrin), driving AP, LacZ, and GM-CSF (62–65).

Construction of second generation type 1 vectors. The generalized construction scheme is to produce the promoter fragment as a PCR product and then to clone it into the AAV gutless/promoterless plasmid dI3-94 (66). The promoter fragment sizes is limited to 500 bp in size. A custom designed multi-cloning site polylinker is ligated into the Bg/II site of dI3-94 to allow for the easy insertion of the promoter, marker gene (AP, LacZ, and GM-CSF gene), and NeoR gene. The resulting vector resembles the AAV/GM-CSF vector.

EXPERIMENT 7

This experiment analyzes the efficiency of second generation-type 1 vector transduction of keratinocytes using AP, LacZ identification assays, and an ELISA assay for secreted GM-CSF. These vectors are compared in raft tissue and in undifferentiated keratinocyte monolayers as well. Equal multiplicities of infection (equal encapsidated genomes) of p5 (first generation) and second generation vetcors are used to infect equivalent general keratinocyte cultures. The expression of AP and LacZ are compared at 2 and 7 days after infection by counting the percent transduction positive cells using the appropriate colorimetric assays described in experiment #1. Higher promoter activity are manifested as a higher percentage of positive cells. GM-CSF secretion are measured by analyzing conditioned medium at 2 and 7 days post-infection by ELISA as described in experiment #1.

The histochemistry assay for AP and LacZ are described in Experiment 1 and the ELISA for GM-CSF secretion is described in Experiment 6.

EXPERIMENT 8

This experiment describes the constructiuon of second generation-type 2 vectors with the AAV p5 promoter replaced with inducible promoters for steroids, glucose and tetracycline, driving AP, LacZ, GM-CSF, and insulin marker genes.

Figure 2:
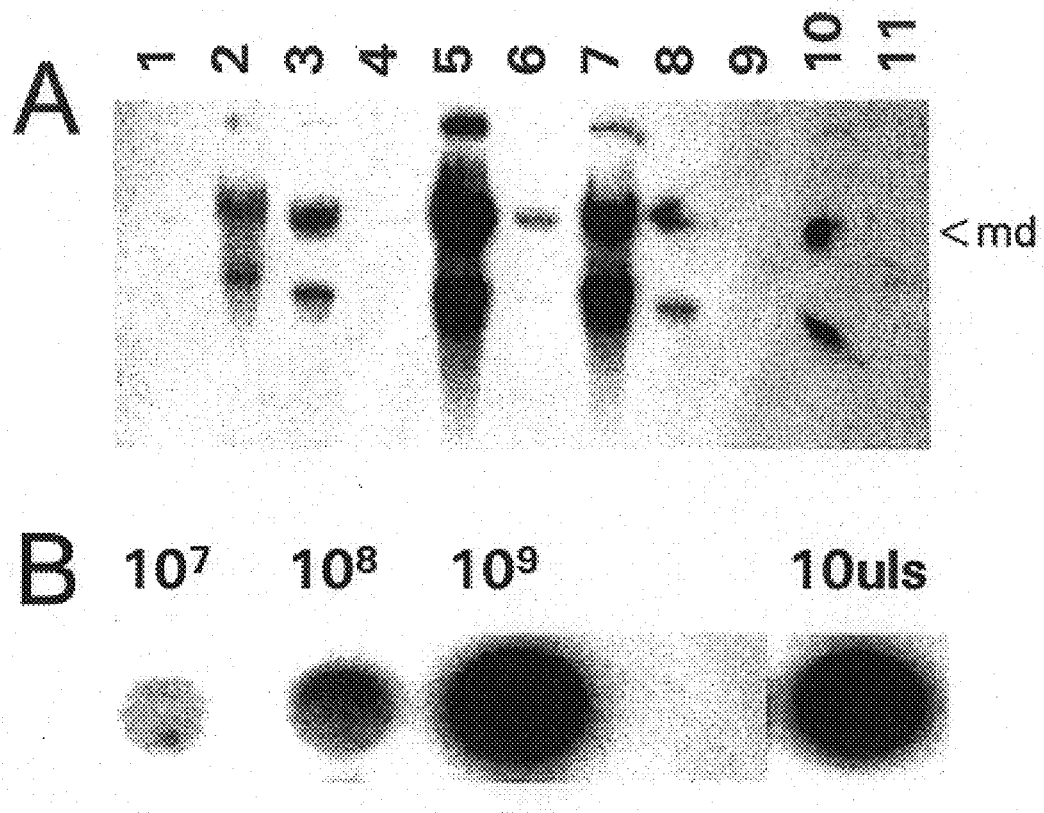
FIG. 2: Generating and titering rAAV virus stocls. A shows a Southern blot of 11 putative producer cell lines as described in the Materials and Methods section below. The blot was probed with $^{32}$P-Neo DNA. Note that 293-AGN clones 5 and 7 produced the highest levels of AAV/p5-GM-CSF/Neo DNA replication. B Shown is a titering dot blot hybridization of the AAV/p5-GM-CSF/Neo virus stock generated from clone 293-AGN-5. On the left are three spots in which $10^7$, $10^8$, and $10^9$ AAV/GM-CSF/Neo plasmid genomes have been applied as titering standards. On the right the DNA from 10 uls of AAV/GM-CSF/Neo virus stock has been applied.

Construction of second generation type 2 vectors. The generalized scheme is identical to that of the construction of the second generation type 1 vectors in experiment #7. The steroid inducible vector is constructed by PCR cloning a subtype Mouse Mammary Tumor Virus (MMTV) promoter which has advantages for our purposes over the standard MMTV. First, the subtype promoter was isolated from an adenocarcinoma (67) and is known to be active in other epithelial cells (68). Second, this promoter was found to be inducible to higher levels of expression by dexamethasone than the wild type MMTV promoter (67,68). The AAV vector plasmid dI3-94 is used as the p5 promoter (as well as all other promoters) has been removed and this promoter is replaced with a steroid-inducible promoter. The GRE-LTR promoter is isolated within a 0.4 Kb region by PCR amplification and then used to construct a dI3-94-GRE-promoter, into which GM-CSF and AP can be ligated. The SV40 promoter-Neomycin resistance gene is also ligated in to allow generation of high titer virus stocks (FIG. 2). Alternatively, the Sh ble or bsd selection gene is used as determined in Experiment 5.

The glucose inducible vectors are constructed by ligating two different glucose response elements into the AAV p5 promoter at the Pml I site (nt 210) site within the p5 promoter of the AAV plasmid dI6-95. One motif, CCAATN$^9$CCACG (SEQ ID NO:1), identified by Yoshida et al. (1999)(40), conferred glucose responsiveness when inserted into promoters. This basic vector is called AAV/glucoseprA. The transcription factor ATF6, identified to be involved in this glucose response pathway is expressed in at least some epithelial cells (41), and appears to be expressed in keratinocytes. Another glucose responsive vector contains the "E box" elements (42, 43), CACGTGN$^3$CAGCTG (SEQ ID NO:2) ligated into the p5 promoter. This basic vector is called (AAV/glucoseprB). The insulin gene is then ligated downstream, and finally the SV40 early promoter-Neomycin cassette is inserted to allow for the generation of high titer virus stocks. Alternatively, the *Sh ble* or *bsd* selection gene is used, as determined in Experiment 5.

A tetracycline inducible vector is be constructed using components from commercially available obtained plasmids. First, one of the small selectable marker genes (Sh ble or bsd, both are 0.4 kb), determined to be the best for keratinocytes in Experiment 3 (does not induce differentiation), is ligated downstream of the p5 promoter (to give, for example, dI6-95/bsd). Then the reverse-tetracycline repressor-VP16 activation domain gene cassette, driven by the cytomegalovirus promoter, (CMVpr-(r)tetR-VP16 AD) is cloned by PCR (1.9 kb) from pTet-On (Clontech, Palo Alto, Calif.) and ligated in the correct orientation behind the bsd gene (to give dI6-95/bsd/CMVpr-(r)tetR-VP16 AD). Next, the tetracycline responsive promoter-multi-cloning site cassette (TREpr-MCS) is also generated by PCR (0.4 kb) from pTRE2 and ligated downstream of the reverse-tet repressor cassette (to give dI6-95/bsd/CMVpr-(r)tetR-VP16AD/TREpr-MCS). The total size of this vector is approximately 3.2 kb. This allows for the insertion of a 1.5 kb marker or therapeutic gene before the wild type AAV size is reached. Therefore, both GM-CSF and insulin are cloned into the MCS of this vector to give a viable vector with a tet-inducible marker or therapeutic gene. It has been determined that, in fact, the virus particle can package genomes which are 1 kb larger than wild type, therefore a maximum size of 2.5 kb might be inserted. The name of the tetracycline inducible vector plus GM-CSF or insulin is too long and is truncated to AAV/TETpr-GM-CSF and AAV/TETpr-insulin. It appears that it will be possible to ligate a selectable marker cassette of small size, such as Sh ble or bsd, as determined in Experiment 5.

EXPERIMENT 9

This experiment analyzes the efficiency of second generation type 2 vector transduction in and transgene regulation in keratinocytes with type 2 vectors with inducible promoters induced by steroids (driving AP and GM-CSF), glucose (driving insulin), and tetracycline (driving GM-CSF).

Analysis of steroid inducible vectors. Transduced general keratinocyte cultures is generated by AAV/GREpr-GM-CSF or AAV/GREpr-APinfection under optimal Experiment 1 conditions. Identical cultures of 60–80% confluent cells.are treated with 0, $10^{-6}$, $10^{-7}$, $10^{-8}$, $10^{-9}$ M dexamethisone for 12 hours, medium collected, and analyzed for GM-CSF as in Experiment #5.

Analysis of glucose inducible vectors. Transduced general keratinocyte cultures are generated by AAV/glucoseprA-insulin or AAV/glucoseprB-insulin infection under optimal Experiment 1 conditions. Identical cultures of 60–80% confluent cells.have the medium replaced with glucose-free DMEM for 6 hrs. The medium is treated with 0, 0.1, 0.5, 1, 5, and 20 mM glucose, and 12 hours later and analyzed for insulin as in Experiment #5.

Analysis of tetracycline inducible vectors. Transduced general keratinocyte cultures are generated by AAV/TETpr-GM-CSF or AAV/TETpr-insulin infection under optimal Experiment 1 conditions. Identical cultures of 60–80% confluent cells.are treated with tetracyclin at 0, 1, 3, 9, 30 µg/ml tetracyclin for 12 hours, medium collected, and analyzed for GM-CSF or insulin levels as in Experiment #5.

EXPERIMENT 10

This experiment analyzes the association of high secretion with rAAV proviral form: episomal (linear or circular (69) or integrated (70,51). Keratinocytes are transduced with AAV/p5-GM-CSF/Neo under optimum conditions determined in Experiment 6. Seven days after infection the total cellular DNA is isolated. Transduction conditions are such that the rAAV copy number per cell will be 1 or higher. Care is taken during isolation so that minimal breakage of DNA will occur (no rough shaking).

Analysis of rAAV DNA by 1D and 2D agarose gel electrophoresis and Southern blotting. For 1 dimensional gel electrophoresis 10 µg of the cellular DNA, uncut, is agarose gel electrophoresed, along with size markers. Two size markers are also be run. One size marker contains a series of DNA fragments increasing by 1000 bp. A second marker is of a plasmid of 3.5 kb in size and contain forms I, II, and III in equal quantities. After running the gel is stained with ethidium bromide and photographed (to align size markers with distance traveled. The gel is then be Southern blotted and probed with GM-CSF and Neo radiolabeled sequences. The size bands giving positive signals is noted. The size provides a good idea as to the form of the provirus. Episomal monomeric linear vector AAV/p5-GM-CSF/Neo DNA is observed at its 3.5 Kb size, and is consistent with 3.5 kb, form III. Any bands seen lower and higher than 3.5 kb, form III are likely to align with forms I and forms II marker DNA and may represent circularized intermediates. Any band seen to be large, greater than 20 kb likely represents chromosomally integrated proviral DNA. It has been observed that a 1.4% agarose band most of the large chromosomal DNA fragments above 20 Kb condenses into a large single band. All of the integrated proviral DNA, no matter how many original transduced clones there are, condensed into this single high band. This high band may contain concatemeric episomal DNA, however such forms are believed to take weeks in forming in muscle.

A similar 2D gel electrophoresis is also performed, Southern blotted, and probed. In this analysis, the forms I, II, and III are present as distinct spots. In contrast, the integrated proviral signal is viewed as a large crescent which coincides with the appearance of the of the high molecular weight genomic DNA crescent.

Analysis by vector-chromosomallyjunctions by PCR amplification/Southern blot. To further analyze for AAV vector chromosomal integration, PCR amplification of vector-chromosomal junctions is carried out in 100 µl reactions using approximately 0.1 µgs of total cellular DNA, 2 mM of each dNTP; 1 µM of each primer and 2.5 U of Taq DNA polymerase according to the supplier's (Fisher Scientific company) instruction, After 5 minute at 94° C., each sample was subjected to following amplification cycle; 50 second at 94° C., 1 minute at 60 ° C. and 2 minutes at 72° C., for 30 cycles, and then 10 minutes at 72° C. Primer 1 was complementary to the SV40 early promoter (5'-GCAGGCAGAAGTATGCAAAG-3'SEQ ID NO:3). Primer 2 (5'-TGCAGGAATTCAGCACAAATTGTAG SEQ ID NO:4), previously characterized by Batzer et al (1991)(77, 96), was complementary to a common human repetitive element, Alu I . After electrophoresis, the reaction products, along with sizing marker DNAs, were directly visualized by ethidium bromide staining and UV fluorescence. The gel was then Southern blotted and probed with $P^{32}$-Neo fragment DNA from pBR-Neo.

Analysis of Recombinant Organotypic Raft Skin (r-skin) Generated from rAAV-infected Keratinocytes to Secrete Transgene Products These studies involve the analysis of the transgene and promoter activity in an r-skin model of normal skin generated from AAV-transduced keratinocytes. It has been shown above, that rAAV/GM-CSF is able to transduce keratinoctyes and that the resulting GM-CSF+/r-skin can secrete GM-CSF over a period of 1 month. These studies are directed to analyzing the conditions to achieve long-term and regulated secretion of GM-CSF, insulin, and factor VIII from skin. Unlike the monolayer keratinocytes, skin is composed of a continum of differentiating keratinocytes. Particularly, the studies focus on the ability of these transduced cells to form a stratified squamous epithelium of r-skin. Furthermore, the expression level of the transgene is closely observed to determine its preferred state of differentiation for expression (second generation type 1 promoters), as well as the overall ability of the total epithelium to produce the product. Three different promoters ("type 1") with preferential activity in three different levels of the skin. K5, HPV-16 p97, and involucrin, and preferentially expressed in the basal, suprabasal, and spinous/granular layers, respectively. Expression in the basal cell layer is believed to allow for higher secretion due to its proximity to the basement membrane. However, the larger cell numbers of the spinous/granular layers may compensate for the greater distance which products must diffuse to leave the skin. Larger proteins, such as factor VIII, may be more effective when expressed in the basal layer, allowing for short diffusion distances.

Finally, the ability of "type 2" promoters to be regulated by exogenous factors when inserted into AAV is also be tested. Such regulatable r-skin allows for a more sophisticated control. Three control elements are inserted into AAV vectors and tested for the retention of control by exogenous diffusing agents. One type of promoter is steroid inducible, and thus steroid applied to the raft induces higher transgene expression. Another type of inducible promoter is a tetracyclin-based promoter. Finally, a third to of promoter is regulatable by high glucose. The glucose response element is ligated nto the AAV p5 promoter and then analyzed for glucose response. The purpose of such a promoter would be for a regulatory scheme which matches insulin's normal regulation as close as possible in skin. The secretion of products and the activity of second generation type 1 and type 2 promoters are analyzed.

EXPERIMENT 11

This experiment analyzes the ability of rAAV/p5-GM-CSF and rAAV/p5-insulin transduced keratinocyte cells to generate recombinant skin (organotypic raft) with high secretory activity and long term secretory activity. The optimal conditions assessed for transducing keratinocytes determined above, are compared again here for ability to produce r-skin which secretes a maximum of transgene product.

Transduction of keratinocytes and generation of recombinant epithelial raft tissue. The rafts are generated from primary human foreskin keratinocytes (PHFK, Clonetics). PHFK is infected with rAAV/p5-GM-CSF and rAAV/p5-insulin or infected and then selected with a selectable marker/cytotoxic agent. The specific techniques and parameters are determined in Experiments 1–10 above are utilized. The transduced keratinocytes (2.5 to $5 \times 10^5$ cells) are seeded on 1 cm diameter collagen rafts containing mouse fibroblast feeder cells as previously published (21,71,72). Once the keratinocyte are attached the submerged collagen raft is raised to the liquid/air interface and then fed every 2 days. At two day intervals the medium from under the rafts is removed, stored at $-80°$ C. and then quantitatively analyzed for GM-CSF and insulin as in Experiment 5. Specimens are collected out to 3 months, or more if possible.

EXPERIMENT 12

This experiment analyzes the histologic region of expression within the skin of first (p5) and second generation (K5, p97, and involucrin) generation vectors expressing AP and LacZ and expression patterns are analyzed.

Generation of recombinant epithelial raft tissue. Keratinocytes are infected with an MOI of $10^3$ genome equivalents of:

| Sub exp A: | rAAV/p5-AP | Sub exp B: | rAAV/p5-LacZ |
|---|---|---|---|
| | rAAV/K5pr-AP | | rAAV/K5pr-LacZ |
| | rAAV/p97-AP | | rAAV/p97-LacZ |
| | rAAV/involucrinpr-AP | | rAAV/involucrinpr-LacZ |

The transduced keratinocytes (2.5 to $5 \times 10^5$ cells) are then seeded on 1 cm diameter collagen rafts containing mouse fibroblast feeder cells as previously published (14,97,98). Once the keratinocyte are attached the submerged collagen raft will be raised to the liquid/air interface and then fed every 2 days.

Histochemical analysis of LacZ and AP activity. Staining for LacZ and AP activity are be carried out as in Experiment 1, and the staining pattern will be observed by cross section histology.

EXPERIMENT 13

This experiment analyzes and compares the ability of first (p5) and second generation-type 1 (K5, p97, and involucrin promoters) vectors to generate recombinant skin (organotypic raft) with high long term transgene secretory activity for both small (GM-CSF and insulin) and large (factor VIII) transgenes.

Transduction of keratinocytes and generation of recombinant epithelial raft tissue. PHFK will be infected with:

Sub exp A: rAAV/p5-GM-CSF
rAAV/K5pr-GM-CSF
rAAV/p97-GM-CSF
rAAV/involucrinpr-GM-CSF Sub exp B: rAAV/p5-factor VIII
rAAV/K5pr-factor VIII
rAAV/p97-factor VIII
rAAV/involucrinpr-factor VIII The keratinocytes are infected with the rAAV vectors using the optimal techniques determined above. The transduced keratinocytes (2.5 to $5 \times 10^5$ cells) are then seeded on 1 cm diameter collagen rafts containing mouse fibroblast feeder cells as previously published (21,71,72). Once the keratinocyte are attached the submerged collagen raft is raised to the liquid/air interface and then fed every 2 days. At two day intervals the medium from under the rafts is removed, stored at $-80°$ C. and then quantitatively analyzed for GM-CSF and factor VIII as in Experiment 5. Specimens are collected out to 3 months or more, if possible.

EXPERIMENT 14

This experiment analyzes and compares the ability of first and second generation-type 2 rAAV (steroid, glucose, and tetracycline inducible) vectors with inducible promoter to generate recombinant skin (organotypic raft) with transgene inducibility short- and long-term.

Transduction of keratinocytes and generation of recombinant epithelial raft tissue. PHFK is infected with AAV/steroidpr-GM-CSF, AAV/glucoseApr-insulin, AAV/tetracyclinpr-GM-CSF or infected and then selected with a selectable marker/cytotoxic agent. The two glucose inducible promoters each contain one of the two different glucose response elements being tested. The specific techniques utilized are those as determined above in the section on transduced keratinocytes. The transduced keratinocytes (2.5 to $5 \times 10^5$ cells) are then seeded on 1 cm diameter collagen rafts containing mouse fibroblast feeder cells as previously published (FF, GG). Once the keratinocyte are attached the submerged collagen raft is raised to the liquid/air interface and then fed every 2 days.

Induction of steroid inducible promoter. Rafts are generated by AAV/steroid pr-GM-CSF infection under optimal conditions for growing transduced keratinocytes above. Identical rafts at day 12 (full thickness) are be treated with 0, $10^{-6}$, $10^{-7}$, $10^{-8}$, $10^{-9}$ M of a steroid to induce the promoter for 12 hours, medium collected, and analyzed for GM-CSF as in Experiment #5.

Induction of glucose inducible promoters. Rafts are generated by AAV/glucoseApr-insulin infection under optimal conditions for growing transduced keratinocytes determined above. Identical rafts at day 12 (full thickness) and the medium are replaced with glucose-free DMEM for 6 hrs. The medium is treated with 0, 0.1, 0.5, 1, 5, and 20 mM glucose, and 12 hours later and analyzed for insulin as in Experiment #5.

Induction of tetracyclin inducible promoter. Rafts are generated by AAV/tetracyclinpr-GM-CSF infection under optimal conditions for growing transduced keratinocytes above. Identical rafts at day 12 (full thickness) are treated with tetracyclin at 0, 1, 3, 9, 30 µg/ml tetracyclin for 12 hours, medium collected, and analyzed for GM-CSF level as in Experiment #5.

Effect of Wild-type AAV on Vector Transduction and Transgene Expression in r-skin The present inventors have shown that wild type AAV (wt AAV) will autonomously replicate in the skin (21), and AAV is a common virus (21). Therefore, it is anticipated that r-skin could be super-infected with wild type AAV (wtAAV) on the patient at a later time. This analysis is directed to the effect that wt-AAV has on rAAV in kerainocytes and raft tissue. The analysis includes studying rAAV activity in skin tissue using the organotypic epithelial raft culture sustem as described in Experiments 11–14 above, but now in the presence of wt AAV.

EXPERIMENT 15

This analysis is directed to studying the efficiency of AAV/p5-AP/Neo and AAV/p5-LacZ transduction of skin rafts generated from general keratinocyte cultures during simultaneous wt type AAV co-infection or delayed wt AAV super infection.

Generation of rAAV + wt AAV simultaneous infection recombinant epithelial raft tissue. Keratinocytes are infected with an MOI of $10^3$ genome equivalents of:AAV/p5-AP/Neo and wt AAV at an MOI of 0, 0.1 , 1, 10, and 100 infectious units/ml. The transduced keratinocytes (2.5 to $5\times10^5$ cells) are then seeded on 1 cm diameter collagen rafts containing mouse fibroblast feeder cells as previously published (21, 71,72). Once the keratinocyte are attached the submerged collagen raft is raised to the liquid/air interface and then fed every 2 days, and fixed and stained for AP activity at days 4 (early epithelium) and 10. (full thickness epithelium).

Generation of rAAV and delayed wt AAV infection infection recombinant epithelial raft tissue. Keratinocytes are infected with an MOI of $10^3$ genome equivalents of:AAV/p5-AP/Neo. The transduced keratinocytes (2.5 to $5\times10^5$ cells) are then seeded on 1 cm diameter collagen rafts containing mouse fibroblast feeder cells as previously published (21,71). Once the keratinocytes are attached, the submerged collagen raft are raised to the liquid/air interface. Wt AAV is applied to the top of identical rafts at various times, at MOI of 0, 0.1, 1, and 10. The times of wt infection is at the initial rise to the air (time 0), and at days 1, 3, and 7. The rafts are fed every 2 days, and fixed and stained for AP activity at days 10.

Histochemical analysis of LacZ and AP activity. Staining for AP activity is carried out as in Experiment #1, and the staining pattern is observed by cross section histology.

EXPERIMENT 16

This experiment analyzes the efficiency of AAV/p5-GM-CSF transduction of skin rafts generated from general keratinocyte cultures during simultaneous wt type AAV co-infection or delayed wt AAV super infection.

This experiment is structured and carried out as in Experiment 15, except for the substitution of AAV/p5-GM-CSF vector and the method of transgene analysis. GM-CSF secretion isa measured as in Experiment 5.

EXPERIMENT 17

This exmperiment analyzes the rAAV proviral form, episomal or integrated, during wildtype AAV infection.

Analysis of rAAV and wtAAV proviral forms. This analysis is carried out as in Experiment 10. However, here probes are used which can distinguish between rAAV and w AAV. Radiolabeled probes of the transgene sequences identifies rAAV and rep/lip-cap sequences will identify wt AAV.

Effectiveness of the Recombinant Skin to Systemically Secrete a Transgene Product in a SCID Mouse Animal Model The ability to show safety and efficacy (significant activity) in SCID mice is a preliminary step for going to clinical trials in human patients. This analysis of r-skin upon grafting onto SCID mice includes the non-exogenously regulated promoters (p5, K5, p97, and involucrin, first and second generation type 1 promoters). These promoters are expressed in different levels of the epithelium. The use of the small transgenes, GM-CSF and insulin, are prototypes for small products, which will more readily diffuse from the skin. The promoters p97 and involucrin, expressed higher in the epithelium and in more cells may be the better promoters for these smaller products. Whereas the K5 promoter, which is expressed in basal cells may be more appropriate for the factor VIII transgene.

A further analysis is the study of r-skin expressing the transgene form second generation type 2 promoters which are designed to be regulated by diffusing facors (steroids, tetracyclin, glucose). This analysis will provide information regarding regulating r-skin which can be turned-on and off when needed. A further analysis studies the alteration of r-skin activity in the presence of wild type AAV. Wild type AAV is applied to r-skin and changes to the skin are observed over time by histology as well as changes in transgene secretion.

These experiments involve the grafting of human transduced keratinocytes onto SCID mice which cannot reject the tissue. The products are then be assayed for in mouse blood. These experiments represent a good pre-clinical model for testing the feasibility of skin gene therapy for secreted products before extending the same protocols to humans in phase I and II clinical trials.

EXPERIMENT 18

This experiment analyzes and compares the ability of various p5 (first generation) and skin-specific promoter (second generation type 1) driven r-skin (from Exp 11 and 13) to secrete transgene product systemically (GM-CSF, insulin, factor VIII) when grafted onto SCID mice.

Grafting of r-skin onto SCID mice. Transduced keratinocytes are generated according to the procedures in Exeripments 1–10 above. The r-skin is grafted onto severe combined immunodeficiency (SCID) mice by the technique described by Choate and Khavari (1997)(71) and Medalie et al. (1996)(72) with minor changes. Briefly described, $2\times10^5$ transduced keratinocytes are seeded onto an acellular dermal sheet (1 cm2)(Cook Biotech Incorp., West Lafayette, Ind.), and allowed to reach full confluence while grown in LT/Gibco Keratinocyte Serum Free Medium (2–5 days). At that time the graft is surgically placed in a wound on the back of the SCID mouse as described (71,72). Five animals are included in each experimental group. There are five groups: four are the four best keratinocyte transduction protocols as grafts and one is untransduced keratinocyte grafts. Animals are assayed at 4 and 8 weeks by obtaining tail vein blood. Finally, the animals will be sacrificed at 6 months.

Determination of transgene product in mouse blood. To measure the levels of transgene product in the mouse serum 0.5 mls of blood is drawn from the animals by tail-vein or retro-orbital bleeding. Serum from the mock grafted animal serves as the negative control. GM-CSF levels are measured using the Sandwich ELISA as in Experiment 3. The factor VIII activity levels are measured using the Stachrom VIII:C kit manufactured by American Bioproducts Corp. Insulin levels are determined by radio-immunoassay (RIA) (CIS, Biointernational, Gif-Sir-Yvette, France). The animals are initially be tested at two weeks post-grafting and then at two week intervals after this. Sshorter intervals of testing may be used if unusual variability in the first grafts is found over time.

EXPERIMENT 19

Analyze and compare the ability of various p5 (first generation) and inducible promoter (second generation type 2) driven r-skin (from Exp 14) to secrete transgene product systemically (GM-CSF or insulin) when grafted onto SCID mice.

This experiment is carried out as in Experiment 18 except the grafts are induced by applying the appropriate inducing agent, steroid or tetracycline, to the graft, or be intravenous injection of glucose. Five animals are included in each experimental group. There are four experimental groups: three are each of the three 2nd generation type 1 vectors from Experiment 9: 1) AAV/TETpr-GM-CSF/Neo, 2) AAV-glucoseprA or B-insulin, and 3) AAV/GREpr-GM-CSF. The final group is untransduced keratinocyte control grafts. Animals treated with these type 2 vectors are assayed at 8 weeks by obtaining tail vein blood. The next day the mice are treated with the appropriate inducing agent (tetracycline, dexamethisone, or glucose [tail vein injected], at the levels placed directly on the graft or injected, and then a blood sample removed one hour later. A week later the animal are tested at a higher level of inducing agent. For tetracycline induction, tetracycline is applied to the graft at levels of 0.1 µg, 1.0 µg, and 10 µg. For dexamethasone induction, 10 ng, 100 ng, and 1 µg of dexamethasone is applied to the graft. For insulin induction, 1 µg, 10 µg, and 100 µg of glucose is injected by tail vein.

EXPERIMENT 20

This experiment analyzes and compares the ability of p5 (first generation) driven r-skin (from Exp 11) to secrete transgene product systemically (GM-CSF) when grafted onto SCID mice and infected with wild type AAV at various MOI.

This experiment is carried out similar to Experiment 18 except that only the AAV/p5-GM-CSF vector is used to generate the skin graft. Furthermore identically generated grafts is infected with wild type AAV in variable amounts and at variable times.

Sub-Experiment A: In sub-experiment A, identical grafts of r-skin are iected with wt AAV at an MOI of 1 at the time of grafting (day 0) and at days 3, 7, and 14. There are five experimental groups. Five animals are included in each experimental group. Four groups are each of the four different AAV infection times. The final group are uninfected keratinocyte grafts. Animals are assayed for GM-CSF in the blood at 3 and 6 weeks by obtaining tail vein blood. Finally, the animals will be sacrificed at 3 months.

sub-Experiment B In sub-experiment B, identical grafts are infected at the time of grafting (time 0) with AAV at an MOI of 0.1, 10, and 1000. There are four experimental groups. Five animals are included in each experimental group. Three groups are each of the three different AAV infection levels. The final group is uninfected keratinocyte grafts. Animals are assayed for GM-CSF in the blood at 3 and 6 weeks by obtaining tail vein blood. Finally, the animals will be sacrificed at 3 months.

Although the invention has been described in detail for the purposes of illustration, it is to be understood that such detail is solely for that purpose and that variations can be made therein by those skilled in the art without departing from the spirit and scope of the invention. The cited publications and documents are herein incorporated in their entirety by reference.

REFERENCE CITATIONS

1) Bantel-Schaal, U., and zur Hausen, H. (1984) *Virology* 134:52–63.
2) Boyce S T. Goretsky M J. Greenhalgh D G. Kagan R J. Rieman M T. Warden G D. *Annals of Surgery*. 222(6):743–52, 1995.
3) Fenjves E S. Gordon D A. Pershing L K. Williams D L. Taichman L B, *Proc.Natl. Acad. Sci.USA*. 86(22):8803–7, 1989.
4) Friedman-Einat M. Grossman Z. Mileguir F. Smetana Z. Ashkenazi M. Barkai G. Varsano N. Glick E. Mendelson E, *J. Clin. Microbiol*. 35(1):71–8, 1997.
5) Georg-Fries, B., Biederlack, S., Wolf J., and zur Hausen, H. (1984) *Virology* 134(1):64–71.
6) Han, L., Parmley, T. H., Keith, S., Kozlowski, K. J., Smith, L. J., and Hermonat, P. L. 1996) *Virus Genes*. 12(1):47–52.
7) Handin, R. I. Disorders of coagulation and thrombosis. in 12th Edition, Harrison's Principles of Internal Medicine. pgs1505–1511, 1990.
8) Hermonat P L. Quirk J G. Bishop B M. Han L FEBS Letters. 407(1):78–84, 1997.
9) Kaufman, R. J. Ann. Hematol. 63:155–165, 1991.
10) Malhomme, O., Dutheil, N., Rabreau, M., Armbruster-Moraes, E., Schlehofer, J. R., and Dupressoir, T. (1997) *Journal of General Virology*. 78 (Pt 8):1957–62.
11) Munster A M. Cultured skin for massive burns. *Annals of Surgery*. 224(3):372–5, 1996.
12) Rennekampff H O. Kiessig V. Hansbrough J F. *Journal of Surgical Research*. 62(2):288–95, 1996.
13) Sabolinski M L. Alvarez O. Auletta M. Mulder G. Parenteau N L. *Biomaterials*. 17(3):311–20, 1996.
14) Samulski R J. Berns K I. Tan M. Muzyczka N.. Proc. Natl. Acad. Sci. USA 79(6):2077–81, 1982.
15) Teumer, J., Lindahl, A., and Green, H. FASEB J. 4: 3245–3250, 1990.
16) Tobiasch, E., Rabreau, M., Geletneky, K., Larue-Charlus, S., Severin, F., Beccker, N., Schlehofer, J. R. (1994) J. Med. Virol. 44:215–222.
17) Toole, J. J., Pittman, D. D., Orr, E. C., Murtha, P., Wasley, L. C., and Kaufman, R. J., Proc. Nati. Acad. Sci. 83:5939–5942.
18) Vogel J C. Keratinocyte gene therapy. [Review] [52 refs]*Archives of Dermatology*. 129(11):1478–83, 1993.
19) Walz, C. M., Anisi, T. R., Schlehofer, J. R., Gissmann, L., Schneider, A. and Muller. M. (1998) *Virology*. 247(1):97–105.
20) Braun-Falco M. Doenecke A. Smola H. Hallek M. (1999) Gene Therapy. 6(3):432–41.
21) Meyers C. Mane M. Kokorina N. Alam S. Hermonat P L. (2000) Virology. 272(2):338–46.
22) Hermonat P L. Plott R T. Santin A D. Parham G P. Flick J T. (1997) Gynecologic Oncology. 66(3):487–94.
23) Atchison, R. W., Casto, B. C., and Hammon, W. M. 1965. Science 194:754.
24) Buller, R. M. L., . . . , and Rose, J. R. 1981 J. Virol. 40:241–247.
25) Hoggan, M. D. 1970. Adeno-associated viruses. Prog. Med. Virol. 12:211–239.

26) Hoggan, M. D., Thomas, G. F., Thomas, F. B., and Johnson, F. B. 1972. Continuous carriage of adeno-assocaited virus genome in cell culture in the absence of helper adenovirus. in: Proceedings of the fourth leprtite colloquium. Cocoyac, Mexico, North-Holland, Amersterdam, pp243–249.

27) Handa, H., Shiroki, K., and Shimojo, H. 1977. Virology 82:84–92.

28) Laughlin, C. A., Cardellichio, C. B., and Coon, H. C. 1986. J. Virol. 60:515–524.

29) Cheung, A. K., Hoggan, M. D., Hauswirth, W. W., and Berns, K. I. 1980. Virol. 33:739–748.

30) Ray M. Mukhopadhyay K. Narang A. (2000) Indian J. Pediatrics. 67(1):67–8.

31) Ravaud A. Chevreau C. Cany L. Houyau P. Dohollou N. Roche H. Soubeyran P. Bonichon F. Mihura J. Eghbali H. Tabah I. Bui B N. (1998) Clinical Oncology. 16(9):2930–6.

32) Bouchama A. Khan B. Djazmati W. Shukri K. (1999) Intensive Care Medicine. 25(9):1003–5.

33) Feng F. Zhou L. (1998) Randomized controlled study of leucomax (recombinant human granulocyte-macrophage colony stimulating factor, rhGM-CSF) in the treatment of cancer chemotherapy-induced leucopenia]. [Chinese] Chung-Hua Chung Liu Tsa Chih [Chinese Journal of Oncology]. 20(6):451–3.

34) Rowe J M. (1998) Clinical Infectious Diseases. 26(6):1290–4.

35) Itala M. Pelliniemi T T. Remes K. Vanhatalo S. Vainio O. (1998) Leukemia & Lymphoma. 32(1–2):165–74.

36) GG. Carr R. Modi N. Dore C J. El-Rifai R. Lindo D. (1999) Pediatrics. 103(4 Pt 1):796–802.

37) Ray M. Mukhopadhyay K. Narang A. (2000) Indian J. Pediatrics. 67(1):67–8.

38) Kavuru M S. Sullivan E J. Piccin R. Thomassen M J. Stoller J K. (2000) Amer. J. Resp. Critical Care Med. 161(4 Pt 1):1143–8.

39) Thule P M. Liu J. Phillips L S. (2000) Gene Therapy. 7(3):205–14.

40) Yoshida H. Haze K. Yanagi H. Yura T. Mori K. (1999) Identification of the cis-acting endoplasmic reticulum stress response element responsible for transcriptional induction of mammalian glucose-regulated proteins. Involvement of basic leucine zipper transcription factors . J Biol Chem 41) Zhu C. Johansen F E. Prywes R. (1997) Molec. Cell. Biol. 17(9):4957–66.

42) Chen R. Meseck M. McEvoy R C. Woo S L. (2000) Gene Therapy. 7(21):1802–1809.

43) Portois L. Maget B. Tastenoy M. Perret J. Svoboda M. (1999) J. Biol. Chem. 274(12):8181–90.

44) Barrandon, Y., and Green, H. (1985) Proc. Natl. Acad. Sci. USA 82:5390–5394.

45) Li, A., Simmons, P. J., and Kaur, P. (1998) Proc. Natl. Acad. Sci. USA 95: 3902–3907.

46) Stockschlaeder M A . . . Miller A D. (1991) Human Gene Therapy. 2(1):33–9.

47) Mauro, T., Dixon, D. B., Hanley, K., Isseroff, R. R., and Pappone, P. A. (1995) J. Invest. Derm. 105:203–208.

48) Oda, Y., Imanzahrai, A., Kwong, A., Komuves, L., Elias, P. M., Largman, C., Mauro, T. (1999) J. Invest. Derm. 113:796–801.

49) Piepkorn, M., Pittelkowm M. R., and Cook, P. W. (1998) J. Invest. Derm. 111: 715–721.

50) Russell D W. Miller A D. Alexander I E. (1994) Procd. Natl. Acad. Sci. USA 91(19):8915–9.

51) Liu Y. Santin A D. Mane M. Chiriva-Internati M. Parham G P. Ravaggi A. Hermonat P L. (2000) J. Interferon & Cytokine Research. 20(1):21–30.

52) Collaco R F. Cao X. Trempe J P. (1999) Gene. 238(2):397–405.

53) Hirt, B. (1967) J. Molec. Biol. 26: 365–9.

54) Southern, E. M. (1975) J. Molec. Biol. 98:503–518.

55) Coker, A. L. . . . Hermonat, P. L. (2001) in press Experimental and Molecular Pathology 56) MacGregor, G., Mogg, A., Burke, J. F., and Caskey, C. T. (1987) Somatic Cell and Molec. Genetics 13:253–265.

57) Blantin, J. R., Grant, A. L., McFarland, D. C., Robinson, J. P., and Bidwell, C. A. (1999) Muscle & Nerve 22: 43–50.

58) Santerre R F. Allen N E. Hobbs J N Jr. Rao R N. Schmidt R J. (1984) Gene. 30(1–3):147–56.

59) Zeocin Dhanvantari S. Brubaker P L. (1998) Endocrinology. 139(4):1630–7.

60) Kumura M. Takatsuki A. Yamaguchi I. (1994) Biochimica et Biophysica Acta. 1219(3):653–9.

61) Pala, P. Verhoef, A. Lamb J. R., Openshaw, P. J. (2000) Immunology. 100(2):209–16, 2000.

62) Casatorres J. Navarro J M. Blessing M. Jorcano J L. (1994) Journal of Biological Chemistry. 269(32):20489–96.

63) Bernard H U. Apt D. (1994) Archives of Dermatology. 130(2):210–5, 1994

64) Welter J F. Eckert R L. (1995) Oncogene. 11 (12):2681–7.

65) Eckert R L. Crish J F. Banks E B. Welter J F. (1997) Journal of Investigative Dermatology. 109(4):501–9.

66) Hermonat, P. L., Labow, M. A., Wright, R., Berns, K. I., and Muzyczka, N. 1984. J. Virology 51(2):329–339.

67) Wellinger, R. J., Garcia, M., Vessaz, A., and Diggelmann, H. (1986) J. Virol. 60:1–11

68) Hirt, R. P., Poulain-Godefroy, O., Billotte, J., Kraehenbuhl, J.-P., and Fasel, N. (1992) Gene 111:199–206

69) Duan D. Sharma P. Yang J. Yue Y. Dudus L. Zhang Y. Fisher K J. Engelhardt J F. (2000) J. Virol. 72(11) :8568–77.

70) Hermonat, P. L., and Muzyczka, N. 1984. Proc. Nati. Acad. Sci. U.S.A. 81:6466–6470.

71) Choate K A. Khavari P A. (1997) Human Gene Therapy. 8(8):895–901.

72) Medalie D A. Eming S A. Tompkins R G. Yarmush M L. Krueger G G Morgan J R. (1996) J. Invest. Derm. 107(1):121–7.

What is claimed is:

1. A method of preparing epithelial cells that express at least one heterologous protein comprising:
   (a) transfecting at least one epithelial cell with a recombinant AAV (rAAV) comprising at least one gene encoding a heterologous protein operably linked to a promoter functional in said epithelial cell; and
   (b) culturing said transfected epithelial cell that expresses said heterologous protein, wherein said culturing results in the production of a sheet of recombinant skin, wherein said sheet comprises a stratified squamous epithelium.

2. The method of claim 1, wherein said epithelial cell is a keratinocyte.

3. The method of claim 2, wherein said keratinocyte is a primary keratinocyte.

4. The method of claim 1, wherein said culturing utilizes the organotypic epithelial raft culture system.

5. The method of claim 1, wherein said promoter is an AAV specific promoter or a skin specific promoter.

6. The method of claim 1, wherein said promoter is an inducible or regulatable promoter.

7. The method of claim 6, wherein said promoter is induced or regulated by exogenous diffusing factors that are capable of diffusing into said recombinant skin.

8. The method of claim 1, wherein said rAAV is integrated into the chromosome of said epithelial cell.

9. A method of producing a heterologous protein in epithelial cells comprising:
   (a) transfecting at least one epithelial cell with a recombinant AAV (rAAV) comprising at least one gene encoding a heterologous protein operably linked to a promoter functional in said epithelial cell;

(b) culturing said transfected epitheilial cell that expresses said heterologous protein, wherein said culturing results in the production of a sheet of recombinant skin, wherein said sheet comprises a stratified squamous epithelium; and (c) expressing said heterologous protein in said epithelial cells in said sheet.

10. The method of claim 9, wherein said heterologous protein is secreted into culture media in which said epithelial cells are cultured.

11. The method of claim 9, wherein said epithelial cell is a keratinocyte.

12. The method of claim 11, wherein said keratinocyte is a primary keratinocyte.

13. The method of claim 9, wherein said culturing utilizes the organotypic epithelial raft culture system.

14. The method of claim 9, wherein said promoter is an AAV specific promoter or a skin specific promoter.

15. The method of claim 9, wherein said promoter is an inducible or regulatable promoter.

16. The method of claim 15, wherein said promoter is induced or regulated by exogenous diffusing factors that are capable of diffusing into said recombinant skin.

17. The method of claim 9, wherein said rAAV is integrated into the chromosome of said epithelial cell.

18. A method of producing a sheet of epithelial cells that express a heterologous protein comprising:

(a) transfecting at least one epithelial cell with a recombinant AAV (rAAV) comprising at least one gene encoding a heterologous protein operably linked to a promoter functional in said epithelial cell;

(b) culturing said transfected epithelial cell that expresses said heterologous protein, whereby a sheet of recombinant skin is formed on a surface within a culture vessel, and wherein said sheet comprises a stratified squamous epithelium; and (c) removing said sheet of recombinant skin from said surface.

19. The method of claim 18, wherein said epithelial cell is a keratinocyte.

20. The method of claim 19, wherein said keratinocyte is a primary keratinocyte.

21. The method of claim 18, wherein said promoter is an AAV specific promoter or a skin specific promoter.

22. The method of claim 18, wherein said culturing utilizes the organotypic epithelial raft culture system.

23. The method of claim 18, wherein said promoter is an inducible or regulatable promoter.

24. The method of claim 23, wherein said promoter is induced or regulated by exogenous diffusing factors that are capable of diffusing into said recombinant skin.

25. The method of claim 18 wherein said rAAV is integrated into the chromosome of said epithelial cell.

26. A sheet of recombinant skin comprising epithelial cells tranfected with recombinant AAV (rAAV) comprising at least one gene encoding a heterologous protein operably linked to a promoter functional in said epithelial cells, wherein said sheet comprises a stratified squamous epithelium.

27. The sheet of claim 26, prepared according to a culturing method comprising the organotypic epithelial raft culture system.

* * * * *